United States Patent
Sweet et al.

(10) Patent No.: US 8,257,968 B2
(45) Date of Patent: Sep. 4, 2012

(54) METHOD AND APPARATUS FOR AUTOMATIC STAINING OF TISSUE SAMPLES

(75) Inventors: Doug Sweet, Santa Barbara, CA (US); Marc Key, Ojai, CA (US); Gordon Feingold, Santa Barbara, CA (US); Kristopher S. Buchanan, Fort Collins, CO (US); Bob Lathrop, San Jose, CA (US); John Favuzzi, Santa Barbara, CA (US)

(73) Assignee: DAKO Denmark A/S (DK)

( * ) Notice: Subject to any disclaimer, the term of this patent is extended or adjusted under 35 U.S.C. 154(b) by 1249 days.

(21) Appl. No.: 10/538,964

(22) PCT Filed: Dec. 19, 2003

(86) PCT No.: PCT/US03/40518
§ 371 (c)(1),
(2), (4) Date: Jun. 14, 2005

(87) PCT Pub. No.: WO2004/058950
PCT Pub. Date: Jul. 15, 2004

(65) Prior Publication Data
US 2006/0088928 A1    Apr. 27, 2006

Related U.S. Application Data

(60) Provisional application No. 60/435,601, filed on Dec. 20, 2002.

(51) Int. Cl.
*C12M 1/34*    (2006.01)
*C12M 3/00*    (2006.01)

(52) U.S. Cl. ............... 435/288.7; 435/286.4; 435/287.3; 422/63; 422/64; 422/65

(58) Field of Classification Search ............... 435/288.7, 435/287.3, 286.4; 422/60, 63, 64, 65
See application file for complete search history.

(56) References Cited

U.S. PATENT DOCUMENTS 3,219,416 A    11/1965   Natelson
(Continued)

FOREIGN PATENT DOCUMENTS

AU      7754191 A1    2/1992
(Continued)

OTHER PUBLICATIONS

U. S. Appl. No. 60/435,601, "Sample Processing Systems and Methods of Sample Processing," filed Dec. 20, 2002, 81 pages.

(Continued)

*Primary Examiner* — William H Beisner
*Assistant Examiner* — Danielle Henkel
(74) *Attorney, Agent, or Firm* — Finnegan, Henderson, Farabow, Garrett & Dunner, LLP

(57) ABSTRACT

The present invention concerns an apparatus (1) for staining tissue samples, said apparatus (1) including a reagent section (2) or reagent containers (3); at least one staining section or tissue samples, a robotic head (22) or robotic element (20) that may move reagent to a predetermined tissue sample, said robotic element (20) being moveable above the reagent and the staining sections, a control element (85) that may manage a staining process, a 2-D optical sensor (86) to detect two-dimensional image data of a relevant property and that can feed the captured image data to the control element (86). By providing the robotic element (20) with a 2-D optical sensor (86), a common image processor may be provided having multiple functions. By using a 2-D optical image processing system, the control system of the apparatus may easily be adapted to read various types of data presentations, just as actual images for sections of the apparatus may be identified in order to assess the condition of the apparatus. The optical sensor may be used to automatically identify the slides and the reagent containers present in the apparatus, just as the optical sensor may be used for checking if a slide is misplaced at or absent from a slide position, etc.

31 Claims, 5 Drawing Sheets

U.S. PATENT DOCUMENTS

| | | | |
|---|---|---|---|
| 3,398,935 A | 8/1968 | Livesey et al. | |
| 3,482,082 A | 12/1969 | Isreeli | |
| 3,513,320 A | 5/1970 | Weldon | |
| 3,547,064 A | 12/1970 | Binnings et al. | |
| 3,553,438 A | 1/1971 | Blitz et al. | |
| 3,600,900 A | 8/1971 | Buddecke | |
| 3,644,715 A | 2/1972 | Holderith | |
| 3,660,638 A | 5/1972 | Oberli | |
| 3,680,967 A | 8/1972 | Engelhardt | |
| 3,772,154 A | 11/1973 | Isenberg et al. | |
| 3,801,775 A | 4/1974 | Acker | |
| 3,807,851 A | 4/1974 | Knox et al. | 353/120 |
| 3,831,006 A | 8/1974 | Chaffin, III et al. | |
| 3,851,972 A | 12/1974 | Smith et al. | 356/72 |
| 3,853,092 A | 12/1974 | Amos et al. | |
| 3,854,703 A | 12/1974 | Gibbs et al. | |
| 3,873,079 A | 3/1975 | Kuus | |
| 3,876,297 A | 4/1975 | Appeldorn et al. | 353/19 |
| 3,909,203 A | 9/1975 | Young et al. | |
| RE28,585 E | 10/1975 | Amos et al. | |
| 3,912,456 A * | 10/1975 | Young | 436/47 |
| 3,916,157 A | 10/1975 | Roulette et al. | |
| 3,916,160 A | 10/1975 | Russo et al. | |
| 3,971,917 A | 7/1976 | Maddox et al. | |
| 3,976,028 A | 8/1976 | Howells et al. | |
| 3,994,594 A | 11/1976 | Sandrock et al. | |
| 4,013,038 A | 3/1977 | Rogers et al. | |
| 4,018,565 A | 4/1977 | Fletcher, III et al. | |
| 4,039,288 A | 8/1977 | Moran | |
| 4,066,412 A | 1/1978 | Johnson et al. | |
| 4,083,638 A | 4/1978 | Sandrock et al. | |
| 4,084,541 A | 4/1978 | Ito | |
| 4,092,952 A | 6/1978 | Wilkie et al. | |
| 4,100,309 A | 7/1978 | Micklus et al. | |
| 4,113,437 A | 9/1978 | Duff et al. | |
| 4,115,861 A | 9/1978 | Allington | |
| 4,133,642 A | 1/1979 | Nosaka et al. | |
| 4,135,883 A | 1/1979 | McNeil et al. | |
| 4,159,875 A | 7/1979 | Hauser | |
| 4,163,643 A | 8/1979 | Hunter et al. | |
| 4,200,056 A | 4/1980 | Johnson | |
| 4,200,607 A | 4/1980 | Suzuki | |
| 4,227,810 A | 10/1980 | Sandrock et al. | |
| 4,245,967 A | 1/1981 | Busselet | |
| 4,263,504 A | 4/1981 | Thomas | |
| 4,281,387 A | 7/1981 | Kraft et al. | |
| 4,286,146 A | 8/1981 | Uno et al. | |
| RE30,730 E | 9/1981 | Duff | |
| 4,298,571 A | 11/1981 | DiFulvio et al. | |
| 4,311,667 A | 1/1982 | Gocho | |
| 4,323,537 A | 4/1982 | Mody | 422/63 |
| 4,338,279 A | 7/1982 | Orimo et al. | |
| 4,346,056 A | 8/1982 | Sakurada | |
| 4,371,498 A | 2/1983 | Scordato et al. | |
| 4,404,641 A | 9/1983 | Bazarnik | |
| 4,406,547 A | 9/1983 | Aihara | |
| 4,447,395 A | 5/1984 | Englar et al. | |
| 4,451,433 A * | 5/1984 | Yamashita et al. | 422/63 |
| 4,455,280 A | 6/1984 | Shinohara et al. | |
| 4,467,073 A | 8/1984 | Creasy | |
| 4,467,603 A | 8/1984 | Wilson | |
| 4,488,679 A | 12/1984 | Bockholt et al. | |
| 4,510,169 A | 4/1985 | Linner | |
| 4,517,160 A | 5/1985 | Galle et al. | |
| 4,528,159 A | 7/1985 | Liston | |
| 4,531,455 A | 7/1985 | Palmer | |
| 4,539,632 A | 9/1985 | Hansen et al. | |
| 4,558,946 A | 12/1985 | Galle et al. | |
| 4,567,748 A | 2/1986 | Klass et al. | |
| 4,571,699 A | 2/1986 | Herzog et al. | 364/900 |
| 4,585,622 A | 4/1986 | Bowe et al. | |
| 4,609,017 A | 9/1986 | Coulter et al. | |
| 4,624,588 A | 11/1986 | Bivin | |
| 4,634,576 A | 1/1987 | Galle et al. | |
| 4,634,850 A | 1/1987 | Pierce et al. | |
| 4,643,879 A | 2/1987 | Hanaway | |
| 4,647,432 A | 3/1987 | Wakatake | |
| 4,647,543 A | 3/1987 | Stöcker | |
| 4,656,006 A | 4/1987 | Assmann et al. | |
| 4,664,526 A | 5/1987 | Scheffler et al. | |
| 4,675,299 A | 6/1987 | Witty et al. | |
| 4,678,752 A | 7/1987 | Thorne et al. | |
| 4,678,894 A | 7/1987 | Shafer | |
| 4,681,741 A | 7/1987 | Hanaway | |
| 4,683,120 A | 7/1987 | Meserol et al. | |
| 4,692,308 A | 9/1987 | Riley et al. | |
| 4,692,603 A | 9/1987 | Brass et al. | |
| 4,695,430 A | 9/1987 | Coville et al. | |
| 4,708,886 A | 11/1987 | Nelson | |
| 4,719,087 A | 1/1988 | Hanaway | |
| 4,727,033 A | 2/1988 | Hijikata et al. | |
| 4,728,783 A | 3/1988 | Brass et al. | |
| 4,728,959 A | 3/1988 | Maloney et al. | |
| 4,729,661 A | 3/1988 | Bell | |
| 4,738,824 A | 4/1988 | Takeuchi | |
| 4,751,186 A | 6/1988 | Baisch et al. | |
| 4,754,127 A | 6/1988 | Brass et al. | |
| 4,761,075 A | 8/1988 | Matsushita et al. | |
| 4,764,342 A | 8/1988 | Kelln et al. | |
| 4,774,055 A | 9/1988 | Wakatake et al. | |
| 4,781,891 A | 11/1988 | Galle et al. | |
| 4,782,221 A | 11/1988 | Brass et al. | |
| 4,794,239 A | 12/1988 | Allais | |
| 4,795,613 A | 1/1989 | Azuma et al. | |
| 4,795,710 A | 1/1989 | Muszak et al. | |
| 4,797,938 A | 1/1989 | Will | |
| 4,800,762 A | 1/1989 | Sugaya | |
| 4,808,380 A | 2/1989 | Minekane | |
| 4,815,978 A | 3/1989 | Mazza et al. | |
| 4,817,916 A | 4/1989 | Rawstron | |
| 4,824,641 A | 4/1989 | Williams | |
| 4,844,887 A | 7/1989 | Galle et al. | |
| 4,847,208 A | 7/1989 | Bogen | |
| 4,849,177 A | 7/1989 | Jordan | |
| 4,855,109 A | 8/1989 | Muraishi et al. | |
| 4,855,110 A | 8/1989 | Marker et al. | |
| 4,865,811 A | 9/1989 | Newton et al. | |
| 4,868,129 A | 9/1989 | Gibbons et al. | |
| 4,869,114 A | 9/1989 | Kido et al. | |
| 4,871,682 A | 10/1989 | Mazza | |
| 4,873,877 A | 10/1989 | Harris | |
| 4,874,936 A | 10/1989 | Chandler et al. | |
| 4,886,590 A | 12/1989 | Tittle | |
| 4,896,029 A | 1/1990 | Chandler et al. | 235/494 |
| 4,900,513 A | 2/1990 | Barker et al. | |
| 4,919,887 A | 4/1990 | Wakatake | |
| 4,924,078 A | 5/1990 | Sant'Anselmo et al. | 235/494 |
| 4,933,147 A | 6/1990 | Hollar et al. | |
| 4,935,875 A | 6/1990 | Shah et al. | |
| 4,939,354 A | 7/1990 | Priddy et al. | |
| 4,939,674 A | 7/1990 | Price et al. | |
| 4,943,415 A | 7/1990 | Przybylowicz et al. | |
| 4,961,906 A | 10/1990 | Andersen et al. | |
| 4,965,049 A | 10/1990 | Lillig et al. | |
| 4,967,606 A | 11/1990 | Wells et al. | |
| 4,985,206 A | 1/1991 | Bowman et al. | |
| 4,986,891 A | 1/1991 | Sarrine et al. | |
| 4,988,482 A | 1/1991 | Weston | |
| 4,998,010 A | 3/1991 | Chandler et al. | |
| 5,031,797 A | 7/1991 | Boris et al. | |
| 5,051,238 A | 9/1991 | Umetsu et al. | |
| 5,053,609 A | 10/1991 | Priddy et al. | |
| 5,059,393 A | 10/1991 | Quenin et al. | |
| 5,068,091 A | 11/1991 | Toya | |
| 5,073,504 A | 12/1991 | Bogen | |
| 5,075,079 A | 12/1991 | Kerr et al. | |
| 5,081,038 A | 1/1992 | Sugaya et al. | 436/46 |
| 5,102,624 A | 4/1992 | Muraishi | |
| 5,104,527 A | 4/1992 | Clinkenbeard | |
| 5,106,583 A | 4/1992 | Raysberg et al. | |
| 5,118,369 A | 6/1992 | Shamir | |
| 5,122,342 A | 6/1992 | McCulloch et al. | |
| 5,124,536 A | 6/1992 | Priddy et al. | |
| 5,180,606 A | 1/1993 | Stokes et al. | |
| 5,202,552 A | 4/1993 | Little et al. | 235/494 |
| 5,225,325 A | 7/1993 | Miller et al. | |
| 5,229,074 A | 7/1993 | Heath et al. | |

| | | |
|---|---|---|
| 5,232,664 A | 8/1993 | Krawzak et al. |
| 5,250,262 A | 10/1993 | Heidt et al. |
| 5,281,395 A | 1/1994 | Markart et al. ............ 422/82.05 |
| 5,289,385 A | 2/1994 | Grandone |
| 5,311,426 A | 5/1994 | Donohue et al. |
| 5,316,319 A | 5/1994 | Suggs |
| 5,316,452 A | 5/1994 | Bogen et al. |
| 5,316,726 A | 5/1994 | Babson et al. |
| 5,316,728 A | 5/1994 | Hayashi et al. |
| 5,322,771 A | 6/1994 | Rybski et al. |
| 5,331,176 A | 7/1994 | Sant' Anselmo et al. |
| 5,338,358 A | 8/1994 | Mizusawa et al. |
| 5,346,672 A | 9/1994 | Stapleton et al. |
| 5,350,697 A | 9/1994 | Swope et al. |
| 5,355,304 A | 10/1994 | DeMoranville et al. |
| 5,355,439 A * | 10/1994 | Bernstein et al. ............ 700/247 |
| 5,355,695 A | 10/1994 | Kawaguchi et al. |
| 5,356,595 A | 10/1994 | Kanamori et al. |
| 5,365,614 A | 11/1994 | Perkins |
| 5,366,896 A | 11/1994 | Margrey et al. |
| 5,369,261 A | 11/1994 | Shamir |
| 5,380,486 A | 1/1995 | Anami |
| 5,382,511 A | 1/1995 | Stapleton |
| 5,395,588 A | 3/1995 | North, Jr. et al. |
| 5,399,316 A | 3/1995 | Yamada |
| 5,417,213 A | 5/1995 | Prince |
| 5,418,138 A | 5/1995 | Miller et al. |
| 5,424,036 A | 6/1995 | Ushikubo |
| 5,425,918 A | 6/1995 | Healey et al. ............ 422/64 |
| 5,428,740 A | 6/1995 | Wood et al. |
| 5,431,455 A | 7/1995 | Seely |
| 5,432,056 A | 7/1995 | Hartman et al. |
| 5,439,645 A | 8/1995 | Saralegui et al. |
| 5,439,649 A * | 8/1995 | Tseung et al. ............ 422/99 |
| 5,439,826 A | 8/1995 | Kontorovich ............ 436/50 |
| 5,446,652 A | 8/1995 | Peterson et al. ............ 364/578 |
| 5,449,622 A | 9/1995 | Yabe et al. |
| 5,473,551 A | 12/1995 | Sato et al. |
| 5,487,975 A | 1/1996 | Miller et al. |
| 5,544,650 A | 8/1996 | Boon et al. |
| 5,549,848 A | 8/1996 | Zeheb et al. |
| 5,552,087 A | 9/1996 | Zeheb et al. |
| 5,573,727 A * | 11/1996 | Keefe ............ 422/63 |
| 5,578,452 A | 11/1996 | Shi et al. |
| 5,580,524 A | 12/1996 | Forrest et al. |
| 5,595,707 A | 1/1997 | Copeland et al. |
| 5,602,674 A | 2/1997 | Weissman et al. ............ 359/393 |
| 5,612,524 A | 3/1997 | Sant'Anselmo et al. ..... 235/494 |
| 5,645,114 A | 7/1997 | Bogen et al. |
| 5,646,046 A | 7/1997 | Fischer et al. |
| 5,646,049 A | 7/1997 | Tayi |
| 5,649,537 A | 7/1997 | Anelli et al. |
| 5,650,136 A | 7/1997 | Platzek et al. |
| 5,650,327 A | 7/1997 | Copeland et al. |
| 5,654,199 A | 8/1997 | Copeland et al. ............ 436/46 |
| 5,654,200 A | 8/1997 | Copeland et al. ............ 436/46 |
| 5,656,493 A | 8/1997 | Mullis et al. |
| 5,675,715 A | 10/1997 | Bernstein et al. ............ 395/32 |
| 5,677,966 A | 10/1997 | Doerrer et al. |
| 5,681,543 A | 10/1997 | Schmitt-Willich et al. |
| 5,695,739 A | 12/1997 | Schmitt-Willich et al. |
| 5,696,887 A | 12/1997 | Bernstein et al. ............ 395/32 |
| 5,723,092 A | 3/1998 | Babson ............ 422/63 |
| 5,733,528 A | 3/1998 | Felder et al. |
| 5,737,449 A | 4/1998 | Lee ............ 382/242 |
| 5,737,499 A | 4/1998 | Bernstein et al. |
| 5,758,033 A | 5/1998 | Bernstein et al. ............ 395/80 |
| 5,776,414 A | 7/1998 | Itani et al. |
| 5,798,092 A | 8/1998 | Schmitt-Willich et al. |
| 5,814,277 A | 9/1998 | Bell et al. |
| 5,820,849 A | 10/1998 | Schmitt-Willich et al. |
| 5,839,091 A * | 11/1998 | Rhett et al. ............ 702/19 |
| 5,854,075 A | 12/1998 | Levine et al. ............ 436/46 |
| 5,875,286 A | 2/1999 | Bernstein et al. ............ 395/82 |
| 5,876,698 A | 3/1999 | Schmitt-Willich et al. |
| 5,885,529 A | 3/1999 | Babson et al. |
| 5,888,576 A | 3/1999 | Nagano |
| 5,888,733 A | 3/1999 | Hyldig-Nielsen et al. ........ 435/6 |
| 5,888,876 A | 3/1999 | Shiozawa et al. |
| 5,900,045 A * | 5/1999 | Wang et al. ............ 95/241 |
| 5,930,461 A | 7/1999 | Bernstein et al. ............ 395/32 |
| 5,945,341 A | 8/1999 | Howard, III ............ 436/46 |
| 5,947,167 A | 9/1999 | Bogen et al. |
| 5,948,359 A * | 9/1999 | Kalra et al. ............ 422/65 |
| 5,958,341 A | 9/1999 | Chu |
| 5,963,368 A | 10/1999 | Domanik et al. ............ 359/396 |
| 5,965,454 A | 10/1999 | Farmilo et al. |
| 5,985,563 A | 11/1999 | Hyldig-Nielsen et al. ........ 435/6 |
| 5,994,071 A | 11/1999 | Ross et al. |
| 6,017,495 A | 1/2000 | Ljungmann |
| 6,019,945 A | 2/2000 | Ohishi et al. |
| 6,045,759 A | 4/2000 | Ford et al. |
| 6,080,363 A | 6/2000 | Takahashi et al. |
| 6,083,490 A | 7/2000 | Ellis et al. |
| 6,092,695 A | 7/2000 | Loeffler |
| 6,093,574 A | 7/2000 | Druyor-Sanchez et al. |
| 6,096,271 A | 8/2000 | Bogen et al. |
| 6,097,995 A | 8/2000 | Tipton et al. |
| 6,104,483 A | 8/2000 | Sebok et al. |
| 6,110,425 A | 8/2000 | Gao et al. |
| 6,110,676 A | 8/2000 | Coull et al. ............ 435/6 |
| 6,142,292 A | 11/2000 | Patterson |
| 6,169,169 B1 | 1/2001 | Hyldig-Nielsen et al. ... 536/72.1 |
| 6,180,061 B1 | 1/2001 | Bogen et al. |
| 6,183,693 B1 | 2/2001 | Bogen et al. |
| 6,192,945 B1 | 2/2001 | Ford et al. |
| 6,193,933 B1 | 2/2001 | Sasaki et al. |
| 6,208,771 B1 | 3/2001 | Jared et al. |
| 6,235,476 B1 | 5/2001 | Bergmann et al. ............ 435/6 |
| 6,244,474 B1 | 6/2001 | Loeffler |
| 6,245,207 B1 | 6/2001 | Yasuda et al. |
| 6,248,590 B1 | 6/2001 | Malachowski |
| 6,281,004 B1 | 8/2001 | Bogen et al. |
| 6,287,772 B1 | 9/2001 | Stefano et al. ............ 435/6 |
| 6,296,809 B1 | 10/2001 | Richards et al. |
| 6,310,179 B1 | 10/2001 | Batz et al. ............ 530/333 |
| 6,327,395 B1 | 12/2001 | Hecht et al. |
| 6,335,208 B1 | 1/2002 | Lowry |
| 6,349,264 B1 | 2/2002 | Rhett et al. ............ 702/19 |
| 6,352,861 B1 | 3/2002 | Copeland et al. ............ 436/46 |
| 6,358,682 B1 | 3/2002 | Jaffee et al. |
| 6,387,326 B1 | 5/2002 | Edwards et al. |
| 6,388,061 B1 | 5/2002 | Bergmann et al. ............ 536/23.1 |
| 6,395,562 B1 | 5/2002 | Hammock et al. ............ 436/518 |
| 6,403,036 B1 | 6/2002 | Rodgers et al. |
| 6,403,931 B1 | 6/2002 | Showalter et al. |
| 6,405,609 B1 | 6/2002 | Richards et al. |
| 6,408,931 B1 | 6/2002 | Tilak |
| 6,414,133 B1 | 7/2002 | Dietz-Band et al. |
| 6,416,713 B1 | 7/2002 | Ford et al. |
| 6,420,916 B1 | 7/2002 | Freeman |
| 6,426,794 B1 | 7/2002 | Trainoff |
| 6,444,170 B1 | 9/2002 | Heid et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,498,037 B1 | 12/2002 | Lewis et al. |
| 6,509,193 B1 | 1/2003 | Tajima |
| 6,534,008 B1 | 3/2003 | Angros |
| 6,537,818 B2 | 3/2003 | Reinhardt et al. |
| 6,541,261 B1 | 4/2003 | Bogen et al. |
| 6,544,798 B1 | 4/2003 | Christensen et al. |
| 6,548,822 B1 | 4/2003 | Morris et al. |
| 6,582,962 B1 | 6/2003 | Richards et al. |
| 6,594,537 B1 | 7/2003 | Bernstein et al. |
| 6,632,598 B1 | 10/2003 | Zhang et al. |
| 6,635,225 B1 | 10/2003 | Thiem et al. |
| 6,699,710 B1 | 3/2004 | Kononen et al. |
| 6,735,531 B2 | 5/2004 | Rhett et al. |
| 6,746,851 B1 | 6/2004 | Tseung et al. |
| 6,800,249 B2 | 10/2004 | de la Torre-Bueno |
| 6,821,072 B2 | 11/2004 | Thiem et al. |
| 6,827,901 B2 | 12/2004 | Copeland et al. |
| 6,855,559 B1 | 2/2005 | Christensen et al. |
| 6,943,029 B2 | 9/2005 | Copeland et al. |
| 7,135,992 B2 | 11/2006 | Karlsson et al. |
| 7,142,852 B2 | 11/2006 | Tell et al. |
| 7,226,788 B2 | 6/2007 | De La Torre-Bueno |

| | | | | | | |
|---|---|---|---|---|---|---|
| 7,303,725 | B2 | 12/2007 | Reinhardt et al. | FR | 2239167 | | 7/1973 |
| 7,378,055 | B2 | 5/2008 | Lemme et al. | GB | 2216 259 | | 3/1988 |
| 7,396,508 | B1 | 7/2008 | Richards et al. | GB | 2218514 | A | 3/2003 |
| 7,400,983 | B2 | 7/2008 | Feingold et al. | JP | 54014287 | A | 2/1979 |
| 7,404,927 | B2 | 7/2008 | Lemme et al. | JP | 55107957 | | 8/1980 |
| 7,850,912 | B2 * | 12/2010 | Favuzzi et al. .............. 422/63 | JP | 63240688 | A2 | 10/1988 |
| 2001/0006417 | A1 | 7/2001 | Modlin et al. | JP | 03209163 | A2 | 12/1991 |
| 2001/0010936 | A1 | 8/2001 | Rizzo et al. | JP | 6504115 | T2 | 5/1994 |
| 2001/0037072 | A1 | 11/2001 | Virtanen | JP | 8500922 | T2 | 1/1996 |
| 2001/0044124 | A1 | 11/2001 | Bacus | JP | 8506888 | T2 | 7/1996 |
| 2001/0049114 | A1 | 12/2001 | Bacus | JP | 9503304 | T2 | 3/1997 |
| 2001/0055799 | A1 | 12/2001 | Baunoch et al. | WO | WO 99/58972 | | 11/1909 |
| 2002/0001849 | A1 | 1/2002 | Copeland et al. .............. 436/46 | WO | WO 8503571 | | 8/1985 |
| 2002/0009391 | A1 | 1/2002 | Marquiss et al. | WO | WO 86/02163 | A1 | 4/1986 |
| 2002/0019001 | A1 | 2/2002 | Light | WO | WO 87/00086 | | 1/1987 |
| 2002/0034456 | A1 | 3/2002 | Ford et al. | WO | WO 87/00280 | A1 | 1/1987 |
| 2002/0072122 | A1 | 6/2002 | Copeland et al. .............. 436/46 | WO | WO 87/06695 | A1 | 11/1987 |
| 2002/0091593 | A1 | 7/2002 | Fowler | WO | WO 88/02866 | | 4/1988 |
| 2002/0098117 | A1 | 7/2002 | Ammann et al. | WO | WO 8802865 | | 4/1988 |
| 2002/0098595 | A1 | 7/2002 | Lubman et al. | WO | WO 89/01616 | | 2/1989 |
| 2002/0110494 | A1 | 8/2002 | Lemme et al. | WO | WO 9113335 | | 9/1991 |
| 2002/0114733 | A1 | 8/2002 | Showalter et al. | WO | WO 92/01919 | | 2/1992 |
| 2002/0116132 | A1 | 8/2002 | Rhett et al. | WO | WO 92/01919 | A1 | 2/1992 |
| 2002/0127727 | A1 | 9/2002 | Bach et al. | WO | WO 93/03451 | | 2/1993 |
| 2002/0176801 | A1 | 11/2002 | Giebeler et al. | WO | WO 93/03451 | A1 | 2/1993 |
| 2002/0177137 | A1 | 11/2002 | Hodge | WO | WO 94/06080 | | 3/1994 |
| 2002/0178547 | A1 | 12/2002 | Shofner et al. | WO | WO 95/10035 | | 4/1995 |
| 2002/0182628 | A1 | 12/2002 | Dietz-Band et al. | WO | WO 95/10035 | A2 | 4/1995 |
| 2003/0003537 | A1 | 1/2003 | Fischer et al. | WO | WO 95/10035 | A3 | 4/1995 |
| 2003/0022391 | A1 | 1/2003 | Richards et al. | WO | WO 95/28179 | A1 | 10/1995 |
| 2003/0032048 | A1 | 2/2003 | Kim et al. | WO | WO 95/32741 | A1 | 12/1995 |
| 2003/0043963 | A1 | 3/2003 | Yamagami et al. | WO | WO 95/33240 | | 12/1995 |
| 2003/0059790 | A1 | 3/2003 | Jaffee et al. | WO | WO 97/23732 | | 7/1997 |
| 2003/0087443 | A1 | 5/2003 | Pressman et al. | WO | WO 97/23732 | A1 | 7/1997 |
| 2003/0099573 | A1 * | 5/2003 | Tseung et al. .............. 422/63 | WO | WO 97/26541 | | 7/1997 |
| 2003/0100043 | A1 | 5/2003 | Kalra et al. | WO | WO 97/26541 | A1 | 7/1997 |
| 2003/0119200 | A1 | 6/2003 | Taft et al. | WO | WO 98/26295 | | 6/1998 |
| 2003/0120633 | A1 | 6/2003 | Torre-Bueno | WO | WO 99/34190 | | 7/1999 |
| 2003/0124729 | A1 | 7/2003 | Christensen et al. | WO | WO 99/34190 | A1 | 7/1999 |
| 2003/0162221 | A1 | 8/2003 | Bader et al. | WO | WO 99/43434 | | 9/1999 |
| 2003/0200111 | A1 | 10/2003 | Damji | WO | WO 99/43434 | A1 | 9/1999 |
| 2003/0215357 | A1 | 11/2003 | Malterer et al. | WO | WO 99/44031 | A1 | 9/1999 |
| 2004/0002163 | A1 | 1/2004 | Reinhardt et al. | WO | WO 99/49295 | | 9/1999 |
| 2004/0033163 | A1 | 2/2004 | Tseung et al. | WO | WO 99/49295 | A1 | 9/1999 |
| 2004/0219069 | A1 | 11/2004 | Kalra et al. | WO | WO 99/55916 | | 11/1999 |
| 2004/0265185 | A1 | 12/2004 | Kitagawa | WO | WO 99/55916 | A1 | 11/1999 |
| 2004/0266015 | A1 | 12/2004 | Favuzzi et al. | WO | WO 99/57309 | | 11/1999 |
| 2005/0038676 | A1 | 2/2005 | Showalter et al. | WO | WO 99/57309 | A1 | 11/1999 |
| 2005/0064535 | A1 | 3/2005 | Favuzzi et al. | WO | WO 00/02030 | | 1/2000 |
| 2005/0124028 | A1 | 6/2005 | Windeyer et al. | WO | WO 00/02030 | A1 | 1/2000 |
| 2005/0159982 | A1 | 7/2005 | Showalter et al. | WO | WO 00/02660 | | 1/2000 |
| 2006/0045806 | A1 | 3/2006 | Winther et al. | WO | WO 00/02660 | A1 | 1/2000 |
| 2006/0046298 | A1 | 3/2006 | Key et al. | WO | WO 00/36393 | | 6/2000 |
| 2006/0063265 | A1 | 3/2006 | Welcher et al. | WO | WO 00/36393 | A2 | 6/2000 |
| 2006/0085140 | A1 | 4/2006 | Feingold et al. | WO | WO 00/77592 | | 12/2000 |
| 2006/0088928 | A1 | 4/2006 | Sweet et al. | WO | WO 01/02859 | | 1/2001 |
| 2006/0088940 | A1 | 4/2006 | Feingold et al. | WO | WO 01/02859 | A1 | 1/2001 |
| 2006/0105359 | A1 | 5/2006 | Favuzzi et al. | WO | WO 01/02861 | | 1/2001 |
| 2006/0148063 | A1 | 7/2006 | Fauzzi et al. | WO | WO 01/02861 | A1 | 1/2001 |
| 2006/0172426 | A1 | 8/2006 | Buchanan et al. | WO | WO 01/04628 | | 1/2001 |
| 2006/0265133 | A1 | 11/2006 | Cocks et al. | WO | WO 0106255 | A | 1/2001 |
| 2007/0010912 | A1 | 1/2007 | Feingold et al. | WO | WO 0106255 | A | 1/2001 |
| 2007/0196909 | A1 | 8/2007 | Showalter et al. | WO | WO 01/07890 | | 2/2001 |
| | | | | WO | WO 01/07890 | A2 | 2/2001 |

FOREIGN PATENT DOCUMENTS

| | | | | | | |
|---|---|---|---|---|---|---|
| | | | | WO | WO 01/51909 | | 7/2001 |
| AU | 0644876 | B2 | 12/1993 | WO | WO 01/51909 | A1 | 7/2001 |
| DE | 4312093 | | 10/1993 | WO | WO 01/55346 | | 8/2001 |
| DE | 4313807 | | 11/1993 | WO | WO 01/55346 | A3 | 8/2001 |
| DE | 69417908 | | 9/1994 | WO | WO 01/68259 | | 9/2001 |
| EP | 0285851 | A2 | 10/1988 | WO | WO 01/68269 | | 9/2001 |
| EP | 0290018 | A2 | 11/1988 | WO | WO 01/68269 | A1 | 9/2001 |
| EP | 0310303 | A1 | 4/1989 | WO | WO 01/75540 | | 10/2001 |
| EP | 0325101 | A1 | 7/1989 | WO | WO 01/87487 | | 11/2001 |
| EP | 0600939 | B1 | 6/1994 | WO | WO 01/87487 | A2 | 11/2001 |
| EP | 0722363 | B1 | 7/1996 | WO | WO 01/87487 | A3 | 11/2001 |
| EP | 0881481 | | 12/1998 | WO | WO 01/88500 | | 11/2001 |
| EP | 0881481 | A1 | 12/1998 | WO | WO 02/056121 | | 7/2002 |
| ER | 0502636 | | 9/1992 | WO | WO 02/064812 | * | 8/2002 |
| ES | 2160486 | | 4/1999 | WO | WO 03/045560 | | 6/2003 |

| | | |
|---|---|---|
| WO | WO 03/045560 A2 | 6/2003 |
| WO | WO 03/045560 A3 | 6/2003 |
| WO | WO 03/052386 | 6/2003 |
| WO | WO 2004/057307 A1 | 7/2004 |
| WO | WO 2004/057308 A1 | 7/2004 |
| WO | WO 2004/058404 A2 | 7/2004 |
| WO | WO 2004/058404 A3 | 7/2004 |
| WO | WO 2004/058950 A1 | 7/2004 |
| WO | WO 2004/059284 A2 | 7/2004 |
| WO | WO 2004/059284 A3 | 7/2004 |
| WO | WO 2004/059287 A2 | 7/2004 |
| WO | WO 2004/059287 A3 | 7/2004 |
| WO | WO 2004/059288 A2 | 7/2004 |
| WO | WO 2004/059288 A3 | 7/2004 |
| WO | WO 2004/059297 A1 | 7/2004 |
| WO | WO 2004/059441 A2 | 7/2004 |
| WO | WO 2004/059441 A3 | 7/2004 |
| WO | WO 2004/074845 | 9/2004 |
| WO | WO 2004/074847 | 9/2004 |
| WO | WO 2005/031312 | 4/2005 |

OTHER PUBLICATIONS

European Patent Application No. 91 90 8695 Supplementary European Search Report, Search completed Mar. 26, 1993, 6 pages.
12 Most Frequently Asked Questions About Thermoelectric Cooling. In: Tellurex Corporation, accessed Oct. 27, 2004, http://www.tellurex.com/12most.html.
Juroshek et al., A High-Power Automatic Network Analyzer for Measuring the RF Power Absorbed by Biological Samples in a TEM Cell, 1984, IEEE, gpo 818-824.
Meldrum et al., Acapella, a capillary-based submicroliter automated sample preparation system for genome analysis, 1999, IEEE, p. 39-48.
Shepard, DNA purification robotics system, 1994, IEEE, gpo 424-425.
Suckau et al., Automation of MALDI-TOF Analysis for Proteomics, 1999, IEEE, p. 1-5.
Histologic, Technical Bulletin for Histatechnology, 2001, Internet, p. 21-44.
Garrett et al., Successful techniques for supporting multidisciplinary science programs with 'ROPOS: 1999, IEEE, p. 753-756.
Office Action dated Apr. 15, 2010, issued in U.S. Appl. No. 10/539,561, filed. Jun. 16, 2005, Key et al.
European Patent Office, Supplemental European Search Report issued in Application EP03814333, mailed Nov. 29, 2011, 3 pages.
European Patent Office, Supplemental European Search Report issued in Application EP03800071, mailed Sep. 14, 2011, 5 pages.
European Patent Office, Supplemental European Search Report issued in Application EP 03808490, mailed Aug. 25, 2011, 4 pages.
Chow et al., "Application of Existing Technology to Meet Increasing Demands for Automated Sample Handling," Clinical Chemistry, 36(9):1579-1582, 1990.
Dricsoll et al., "Discreet Automated Chemistry System with Tableted Reagents," Clinical Chemistry, 29(9): 1609-1615, 1983.
Garza et al., "Bar Codes in the Clinical Laboratory," Clinical Laboratory Science, 4(1):23-24, Jan./Feb. 1991.
Innis et al., "DNA Sequencing with *Thermus aquaticus* DNA Polymerase and Direct Sequencing of Polymerase Chain Reaction-Amplified DNA," Proc. Natl. Acad. Sci, 85:9436-9440, Dec. 1988.
International Application No. PCT/US03/40880 Written Opinion dated Sep. 28, 2005.
Lindeman et al., "Evaluation of the Automation of the Immunoenzymatic Procedures in a Routine Histo/Cytopathalogical Laboratory," Histopathology, 6:739-746, 1982.
Rappaport, "If Bar Code Works in Supermarkets, It Should Be Great for Medicine,"Pathologist, 39(2): 39-40, 185, Feb. 1985.
Saiki et al., "Enzymatic Amplification of β-Globin Genomic Sequences and Restriction Site Analysis for Diagnosis of Sickle Cell Anemial," Science 230:1350-1353, Dec. 20, 1985.
Stark et al., an automated Devide of Immunocytochemistry, Journal of Immunological Methods, 1988, Elsevier, 107, pp. 89-92.
Tilzer et al., "Use of Bar Code Labels on Collection Tubes for Specimen Management in the Clinical Laboratory," Arch Pathol Lab Med, 112:1201-1202, Dec. 1988.
U.S. Appl. No. 10/054,535, Entitled Automated Biological Reaction Apparatus , now Patent No. 6,943,029.
U.S. Appl. No. 07/488,601, "Automated Biological Reaction Apparatus" filed Mar. 2, 1990.
U.S. Appl. No. 07/924,052, "Automated Biological Reaction Apparatus" filed Aug. 31, 1992.
United States District Court, District of Arizona, *Ventana* v. *Cytologix*, CIV 02117 TUC(WDB) Defendant's Surreply in Opposition to Plaintiffs Motion for Preliminary Injunctive Relief filed Jul. 2002.
United States District Court, District of Arizona, *Ventana* v. *Cytologix*, CIV02117 TUC (RCC) Plaintiffs Motion for Temporary Restraining Order filed Mar. 2002.
United States District Court, District of Arizona, *Ventana* v. *Cytologix*, CIV 02117 TUC (RCC) Plaintiffs Memorandum in Support of Petition for Temporary Restraining Order and Permanent Injunction filed Mar. 2002.
United States District Court, District of Arizona, *Ventana* v. *Cytologix*, CIV 02117 TUC (WDB) Ventana's Reply in Support of its Motion for Preliminary Relief filed Jun. 2002.
United States District Court, District of Arizona, CV03-92 TUC-RCC, *Ventana Medical* vs *Biogenix Laboratories*, Order and Opinion on Motion, Aug. 23, 2005.
United States District Court, District of Arizona, CV03-92 TUC-RCC, *Ventana Medical* vs *Biogenix Laboratories Reporter's Transcript of Proceedings* (*Markman Hearing*) before Honorable Raner C. Collins, Aug. 11, 2005.
United States District Court, District of Arizona, CV03-92 TUC-RCC, *Ventana Medical* vs *Biogenix Laboratories*, Order filed Oct. 4, 2005.
United States District Court, District of Arizona, CV03-92 TUC-RCC, *Ventana Medical* vs *Biogenix Laboratories*, Judgment in a Civil Case, Oct. 19, 2005.
United States District Court, District of Delaware, *Ventana* v. *Dakocytomation California*, CIV041522 (GMS) Order Construing the Terms of U.S. Patent No. 6,827,901 dated Dec. 13, 2005.
United States District Court, Eastern District of Massachusetts, *Vision Biosystems (USA) Trading* v. *Ventana Medical Systems*, CIV 03CV10391GAO, Defendant's Statement of Undisputed Material Facts, in Support of its Cross-Motion for Summary Judgment of Infringement of the 861 Patent filed Jan. 2004.
United States District Court, Eastern District of Massachusetts, *Vision Biosystems (USA) Trading* v. *Ventana Medical Systems*, CIV 03CV10391GAO, Defendant's Memorandum in Opposition to Plaintiffs Motion for Summary Judgment of No Infringement, and in Support of Defendant's Cross-Motion for Summary Judgment of Infringement of the 861 Patent, filed Jan. 15, 2004.
United States District Court, District of Massachusetts, *Vision Biosystems (USA) Trading* v. *Ventana Medical Systems*, CIV 03CV10391GAO, Defendant's Statement of Material Facts in Dispute, in Opposition to Plaintiffs Motion for Summary Judgment of No Infringement of the 861 Patent, filed Jan. 15, 2004.
United States District Court, District of Massachusetts, *Vision Biosystems (USA) Trading* v. *Ventana Medical Systems*, CIV 03CV10391GAO, Memorandum and Order filed Sep. 30, 2004.
United States District Court, District of Massachusetts, *Vision Biosystems (USA) Trading* v. *Ventana Medical Systems*, CIV 03CV10391GAO, Plaintiffs motion for Summary Judgment of Non-Infringement Based on Collateral Estoppel filed Oct. 7, 2005.
United States District Court, District of Massachusetts, *Vision Biosystems (USA) Trading* v. *Ventana Medical Systems*, CIV 03CV10391GAO, Plaintiffs Statement of Undisputed Facts in Support of its Motion for Summary Judgment of Non-Infringement Based on Collateral Estoppel, filed Oct. 7, 2005.
United States District Court, District of Massachusetts, *Vision Biosystems (USA) Trading* v. *Ventana Medical Systems*, CIV 03CV10391GAO, Plaintiffs Memorandum in Support of its Motion for Summary Judgment of Nonfringement Based on Collateral Estoppel, filed Oct. 7, 2005.
United States District Court, District of Massachusetts, *Vision Biosystems (USA) Trading* v. *Ventana Medical Systems*, CIV 03CV10391GAO, Declaration of Richard Wydeven in Support of Plaintiffs Motion for Summary Judgment of Non-Infringement Based on Collateral Estoppel, filed Oct. 7, 2005.

United States District Court, District of Massachusetts, *Vision Biosystems (USA) Trading v. Ventana Medical Systems*, CIV 03CV10391GAO, Defendant Ventana Medical Systems, Inc.'s Memorandum in Opposition to Vision's Motion for Summary Judgment of Non-Infringement Based on Collateral Estoppel, filed Oct. 21, 2005.

United States District Court, District of Massachusetts, *Vision Biosystems (USA) Trading v. Ventana Medical Systems*, CIV 03CV10391GAO, Defendant Ventana Medical Systems, Inc.'s Statement of Material Facts in Dispute, in Opposition to Vision's Motion for Summary Judgment of Non-Infringement Based on Collateral Estoppel, filed Oct. 21, 2005.

International Preliminary Examination Report, International Application No. PCT/US03/40519 filed Dec. 19, 2003.

International Preliminary Examination Report, International Application No. PCT/US03/40591 filed Dec. 19, 2003.

International Preliminary Examination Report, International Application No. PCT/US03/40518 filed Dec. 19, 2003.

International Preliminary Examination Report, International Application No. PCT/US03/40880 filed Dec. 22, 2003.

International Preliminary Examination Report, International Application No. PCT/US03/00877 filed Dec. 15, 2003.

International Preliminary Examination Report, International Application No. PCT/US03/41022 filed Dec. 22, 2003.

International Preliminary Examination Report, International Application No. PCT/US03/40520 filed Dec. 19, 2003, mailing date Mar. 27, 2006.

Written Opinion, International Application No. PCT/US03/40520 filed Dec. 19, 2003.

International Preliminary Examination Report, International Application No. PCT/US03/40520 filed Dec. 19, 2003, mailing date May 31, 2005.

Written Opinion, International Application No. PCT/US03/40974 filed Dec. 19, 2003.

International Preliminary Examination Report, International Application No. PCT/US03/40974 filed Dec. 19, 2003.

U.S. Appl. No. 60/487,998, filed Jul. 17, 2003, "An Interface Point Server".

U.S. Appl. No. 11/119,417, filed Apr. 30, 2005, Method and Apparatus for Pretreatment of Biological Samples.

Taylor, C., Creating a bar code chemistry system, Medical Laboratory Observer, Feb. 1993;25(2):34-6.

Singer, R. et al., Selection and evaluation of laboratory instrumentation in clinical chemistry: II Guidelines for selection and evaluation, Med Lab Sci. Jan. 1987;44(1):6-14.

Rocks, B. F. et al., Automatic analysers in clinical biochemistry, B F Rocks et al 1986 Clin. Phys. Physiol. Meas. 7 1-29.

Pearson, L. S., The use of bar coding technology, Medical Device Technology, Mar. 1994.

Lifshitz, M. S, et al., Talking about Technology, Clinical Laboratory Management Review, Jan.-Feb. 1989;3(1):53-4.

Supplementary European Search Report, EP 0539379A4 entitled "Automatic Tissue Staining for Immunohistochemistry," 4 pages, Mar. 1993.

U.S. Appl. No. 11/119,417, filed Apr. 30, 2005, entitled "Method and Apparatus for Pretreatment of Biological Samples," 39 pages.

U.S. Appl. No. 11/156,760, filed Jun. 20, 2005, entitled "Method and Apparatus for Automated Pre-Treatment and Processing of Biological Samples," 126 pages.

PCT/US2005/006383 filed Feb. 28, 2005, entitled "Reagent Delivery System, Dispensing Device and Container for a Biological Staining Apparatus," 56 pages.

International Preliminary Examination Report PCT/US03/40880, Dec. 2005.

* cited by examiner

METHOD AND APPARATUS FOR AUTOMATIC STAINING OF TISSUE SAMPLES

This application is the United States National Stage of International Application No. PCT/US2003/040518, filed Dec. 19, 2003 which claims the benefit under 35 U.S.C. 119(e) of U.S. Provisional Application No. 60/435,601, filed Dec. 20, 2002, each hereby incorporated by reference herein.

TECHNICAL FIELD

The present invention relates to an apparatus and a method for automatic staining of tissue samples. It may further relate to systems for sample processing and data acquisition, data maintenance, and data retrieval for sample processing. Applications to which the present invention may especially relate include immunohistochemistry, in-situ hybridization, fluorescent in-situ hybridization, special staining, and cytology, as well as potentially other chemical and biological applications.

BACKGROUND

Tissue sample processing in immunohistochemical (IHC) applications and in other chemical and biological analyses, such as in-situ hybridization, special staining and cytology, may require one or more processing sequences or protocols as part of an analysis of one or more samples. The sample processing sequences or protocols may be defined by the individual or organization requesting an analysis, such as a pathologist or histologist of a hospital, or may be defined by dictates of a particular analysis to be performed, e.g. standardized protocols defined by an organization.

In preparation for sample analysis, a biological sample may be acquired by known sample acquisition techniques and may comprise tissues which in some applications may even be one or more isolated cells. The tissue sample may be accommodated on a sample carrier such as a slide or perhaps a microscope slide.

For example, immunologic applications may require processing sequences or protocols that comprise steps such as deparaffinisation, target retrieval, and staining. Previously, in some applications, these steps may have been performed manually, potentially resulting in a time consuming protocol and necessitating personnel to be actively involved in sample processing. In particular relating to the staining process, various devices for automated staining of tissue slides are known, as attempts have been made to automate sample processing to address the need for expedient sample processing and less manually burdensome operation.

Aspects of the present invention may be especially applicable to sample processing having one or a plurality of processing steps to be performed on one, a portion, or an entirety of samples, such protocols identified in some instances by the individual carriers presenting the samples. Aspects of the present invention may be especially applicable to immunohistochemistry (IHC) techniques, as well as in-situ hybridization (ISH) and fluorescent in-situ hybridization (FISH), especially techniques incorporating the staining of samples.

Embodiments of the invention may further relate to automated control systems for sample processing. Embodiments may also be directed to data acquisition, data maintenance, data retrieval for sample processing, especially information sharing of processing protocol and processing status, such as for individual samples or multiple batch processing, sample diagnostic features, and real-time or adaptive capabilities for multiple batch processing.

U.S. Pat. No. 5,839,091 discloses an apparatus for automatic tissue staining where microscope slides are arranged in a number of rows and reagent vials are stored in a section next to this slide section. A robotic head picks up a predetermined amount of reagent from a bottle and deposits this amount of reagent on a predetermined slide and blows the liquid off the slides according to a control program. This program is run on a computer that is coupled to the staining apparatus. The apparatus is loaded with a number of slides, and each slide and its position is registered in the computer and a staining sequence is selected. The program also receives data relating to the reagents and their position in the reagent section. On the basis of these slide and reagent position data, the program calculates a staining run and controls the robotic motion in the apparatus.

U.S. Pat. No. 6,352,861 discloses a carousel-type automatic staining apparatus in which the slides are arranged on a rotatable carousel slide support and the reagents are similarly arranged on a rotatably carousel reagent support above the slide support. A particular slide is then rotated to a delivery zone and a particular reagent vial is also rotated to this position and reagent is dispensed onto the slide. The slides and the reagent bottles are provided with bar codes and associated bar code readers are provided to identify the slides and the reagents respectively. A blowing zone and an identifying zone are also provided at the periphery of the slide carousel. The slide bar codes identify the slide samples and their particular immunohistochemical processes required for the particular samples. A reagent bar code reader is positioned to scan the reagent bar codes on the reagent bottles. The scanned information from the slide bar code reader and the reagent bar code reader is fed into a computer and correlated with the indexed position of the slide and the reagent carousel, respectively. This information is used to rotate the slide carousel and the reagent carousel to place the correct reagent bottle in the dispense zone for each slide treatment step for each slide.

A drawback of the automated staining apparatus described in '091 is that the position of each of the tissue slides and each of the reagent vials in the slide section and in the reagent section, respectively, must be entered manually into the computer, since the control program cannot check the location of the particular slides and reagent vials. This involves the risk that a misplaced slide is treated with the wrong staining protocol and makes the apparatus very inflexible in use.

Although the '861 patent uses a bar code identification of the slides and reagents, this carousel-type apparatus is time consuming in running the staining protocols, since this involves rotating the carousels with the entire reagent inventory and the slide carousel with all the slides for each step in a protocol. These rotations are time consuming and make this type of apparatus unsuitable for running of larger numbers of slides. Moreover, the bar codes can only carry a small amount of data, typically simply an identification code, which means that the control computer must be provided with corresponding data associated with the identification codes.

DISCLOSURE OF INVENTION

It is an object for the present invention to provide an automatic tissue sample processing apparatus of the initially mentioned kind, with automatic identification of the inventory of reagents and slides present in the machine. Another object is to provide identification of relevant properties of the apparatus to allow for automatic preparatory checks before a staining process of newly loaded slides is initiated.

In one embodiment these objects are achieved by an apparatus of the initially mentioned kind wherein a robotic element, perhaps with a robotic head, is provided with an optical sensor, or perhaps a 2-D optical sensor means for detecting two-dimensional image data of a relevant property and with the capability of feeding the captured image data to the control means.

The invention also provides a method of identifying at least one property in an automatic staining apparatus perhaps including at least one slide array and a reagent array and a robotic element or perhaps robotic means for performing staining of the slides also using reagents;
  said method including in one embodiment the steps of
    providing optical sensor means on the robotic head of the robotic means,
    moving the optical sensor means on said robotic head to a predetermined position,
    recording relevant image data at said position, and
feeding said image data to a control system for manipulating the staining process according to said image data.

Furthermore, the invention concerns a method of staining tissue samples in an automatic staining apparatus perhaps including at least one slide array and a reagent array, a robotic element or perhaps and robotic means for performing staining of the slides also using reagents according to tissue sample specific staining protocols; said method including in one embodiment the steps of:
  providing optical sensor means on the robotic head of the robotic means,
  moving the optical sensor means on said robotic head to a predetermined position,
  recording relevant image data at said position by said optical sensor means;
  feeding said image data to a control system for manipulating the staining process according to said image data; and
staining a tissue sample also using reagent from a reagent container.

In embodiments, the automatic staining apparatus 1, that is any apparatus that stains with at least some automated operation, may include a reagent container 3. One or more reagent containers 3 may be positioned in a reagent section 2 of the automatic staining apparatus 1. The automatic staining apparatus may also include a tissue sample 74 which may therein be placed on a slide. A plurality of slides with tissue samples thereon may also be positioned in a slide section 5 of the automatic staining apparatus 1. The invention, in embodiments, may also include a robotic element 20, some type of control element, and even an optical sensor (86), perhaps an image-capture 2-D optical sensor. As can be easily understood, the control element 85, may be a computer, software routine, or merely a particular programmable processor functionality.

As mentioned, the present invention may provide for the capability of optically sensing a two dimensional image. This can occur through an image-capture 2-D sensor which may provide a two-dimensional image of an element in the auto staining apparatus 1. Through providing the robotic element or perhaps a robotic head with a 2-D optical sensor or means, as but one embodiment, a common image processing means is able to have multiple functions. By using a 2-D optical image processing system, the control system of the apparatus may easily be adapted to read various types of data presentations, just as actual images of elements or for sections of the apparatus may be identified in order to assess the condition of the apparatus. The optical sensor or optical sensor means may be used to automatically identify the slides and the reagent containers present in the apparatus, just as the optical sensor or optical sensor means may be used for checking if a slide is misplaced at or absent from a certain slide position, etc.

An optical sensor provides a staining apparatus according to the invention with a hitherto unseen flexibility and possibility of automating the identification functions in a staining apparatus. By utilizing a CCD-camera or the like, perhaps on the robotic head or even the robotic element, individual identification means for each of the identification tasks may no longer be required. This means that controlling as well as maintenance of the apparatus is facilitated. The software controlling the apparatus may be adapted to include automated identifications of various properties and conditions of the apparatus, including slide and reagent information. By a method of identifying relevant properties in the staining apparatus and a method of performing the staining process according to the invention, the automated staining process may be less time-consuming and more qualitative checks may be included without loosing any significant speed in the slide staining operations.

In one embodiment of the invention, the reagent section accommodates a plurality of reagent containers stationary arranged in a plurality of rows. Similarly, the tissue samples are accommodated on slides that are stationary arranged in a plurality of rows in the at least one staining section or slide section during the staining process. The layout of these sections is such that it presents a substantially planar platform work area for the robotic head, which is moveable in the X and Y-axis. In a particularly preferred embodiment, a row of slides and/or reagents can be removed and be replaced without interfering with the staining process.

In another preferred embodiment, the apparatus comprises at least two staining sections separated by a reagent section, that is they may be arranged so that at least some of the tissue samples are closer to at least some of the reagent containers. Hereby, the movements required by the robotic head in order to reach all the slides may be significantly limited and the capacity of the staining apparatus can hereby be increased, just as a reduction in the time for running the staining protocols or other advantages may be achieved. It is further realized that these shorter processing times or other advantages may also be achieved by this layout of the slide and reagent sections without a vision system, e.g. an optical sensor.

In other preferred embodiments of the invention, the optical sensor may be a camera or perhaps include a CCD element. By the term "camera" it should be understood that any image capture apparatus is intended whether or not is uses film, plates, memory, or any type of electronic media and whether or not it images light, visible electromagnetic radiation, or even non-visible electromagnetic radiation such as now well known. By recording the relevant image, relevant image data, or even recording digital image data, a computer processing of this data in the control system may be carried out in a quick manner by known image processing capabilities already available. Moreover, by using this digital technology relative complex images can be recorded with high resolution, just as a fast recording of several identifications, e.g. labels on an entire row of slides, may be achieved as the robotic head may be moved across the slide labels in a continuous movement, so stop and start time for each slide identification may be avoided. However, by the invention it is realized that other image sensors, e.g. solid state sensors, or perhaps CMOS sensors could also be used depending on the requirements for image resolution.

As indicated above, the optical sensor may be adapted to record the individual reagent containers or bottles and slides present in the apparatus. While of course it may image larger areas, or perhaps even the entire device, it may be configured for individual imaging either electronically, optically, or positionally. Regardless, as a result of the imaging capability, predetermined positions of the slides or reagent containers or bottles that are loaded into the automatic staining apparatus may not be required, since the apparatus may be adapted to automatically identify new slides and reagent bottles once they are loaded into the apparatus.

In an embodiment, the reagent containers and the slides may be provided with an optical identification element. For example, a reagent container may be provided with a reagent optical identification element and a slide may be provided with a slide optical identification element. These optical identification elements may contain machine readable data concerning the reagent type as well as other relevant data relating to the reagent in the bottle, and the slide identifiers may contain data concerning the tissue sample, such as identification of the patient, the staining protocol, etc. An optical identification element may include reiterated information or perhaps even redundant information. This may include information that is repeated or even partially repeated and may even include information that may or may not be in different versions which may relate to similar information.

The optical identification element or alternatively optical identification means may be on or even mounted on the reagent container or on the slides in such a manner that the optical identification element is readable by the optical sensor. By being positioned "on" it is intended that any manner of association be encompassed; thus it should be understood that separate attachment or surface mounting is not required. Similarly, by being "above" it should be understood that this may exist not only in a sense such as with respect to gravity, but also in a figurative sense such as roughly perpendicularly above a surface or the like. In an embodiment, the optical identification element may be readable from above by the optical sensor or alternatively means. Furthermore, the optical identification element may be provided on a label, which is perhaps adhesively attachable to a specific slide or reagent bottle. Hereby, the labels or perhaps adhesive labels may be presented to the optical sensor means on the robotic head above the slides and the reagent bottles facilitating the reading of the optical identification means. By providing the optical identification means on a printed label which is attached to the slide, respectively the reagent bottle, individual labels may be prepared on site and the relevant data may be entered into a computer and a corresponding label carrying said relevant data may be printed on an associated label printer.

In an embodiment of the invention, one type of optical identification element may be a two-dimensional high-resolution symbology code, e.g. of the so-called "INFOGLYPH™" type. The optical identification may also be more generically a two-dimensional symbology. Two-dimensional symbology may be representative of data including, but not limited to: tissue sample related data, patient identification data, staining protocol data, reagent related data, regent type data, regent volume related data, regent durability related data, and the like data. By encoding the relevant information into numerous tiny, individual graphic elements, typically small lines in 45° diagonal lines as short as 0.02 mm (1/100 inch), a high resolution with high contrast encoded information label may be achieved which is printable in a printer and readable by a high resolution camera. The type of encoded 2-D symbology label may be provided in different colors and in a variety of materials.

Alternatively, the optical identification means or alternatively the optical identification element may be a data matrix code or even a one-dimensional bar code, namely the identification code with a pattern of vertical bars whose width and spacing identifies an item marked. An advantage of using an optical sensor capable of reading 2-D symbology is that the apparatus may be capable of reading any kind of optical identifier, as this is only requires an adaptation in the software processing the captured perhaps digital image.

In an embodiment, an optical identification element label may include a two-dimensional (2-D) symbology zone and even at least one human readable text zone, each as conceptually depicted in FIG. 5. Hereby, an extra visual inspection of the label by the operator may be provided for verification of the printed label.

In a more advanced usage of the 2-D image capturing capability, the image processing capability or image processor element may be adapted to identify the texture or outline of the tissue sample itself captured by the optical sensor and may use said image-captured tissue property as an individual identification of the tissue sample. The optical sensor may be configured to identify desired features of the tissue samples such as but not limited to the texture, outline, a visual property, or even an individual feature of a tissue sample. Of course, various different features or properties may be identified as desirable to detect or perhaps identify, a property which may include any attribute, characteristic, or the like. This embodiment could make the use of slide labels obsolete, as the tissue texture itself or at least a predefined section thereof (with or without magnification) could be used as an identifier for a list of data in the control software.

In one preferred embodiment of the invention, the optical sensor may be a moveable optical sensor which may be moveable along the areas above the staining and the reagent sections, and said optical sensor may be adapted to determine the presence of and the positions of slides in the at least one staining section. This may be facilitated by having the optical sensor movable in response to or perhaps on a robotic element. Once a new set of slides are being loaded into the apparatus, this feature would allow the staining apparatus according to this embodiment of the invention to automatically determine where the slides are positioned so that the optimal scheduling of treatment steps can be calculated. The optical sensor may even determine the approximate location and the approximate area of a tissue sample. Furthermore, this capability may also provide the apparatus control software with warning if a slide is not correctly positioned or other irregularities have occurred during the loading of the slides.

In another embodiment of the invention, the optical sensor may be adapted to locate pre-selected reference locations for self-calibration of the robotic control system or robotic element controlling the movements of the robotic head. The camera can be used to teach the robotic arm critical locations necessary to calibrate the system, allowing the apparatus to properly position the robotic head to all required positions and locations within the platform work area. If the apparatus has been moved or otherwise been tampered with, e.g. due to maintenance, etc., this feature may provide the staining apparatus according to the invention with the capability of self-calibrating the robotic motion control system, e.g. if the slides are arranged in racks (intended to broadly encompass any locationally tied collection) by checking if the slide rack fit correctly into a receiving element in the apparatus, and/or by determining the position of predefined reference components of the apparatus.

In another embodiment of the invention, the optical sensor may be a camera adapted to record an image of the finalized tissue sample after said tissue sample has been subjected to a staining protocol for recording an image of the manipulated tissue sample. Hereby, a picture or digital image of the stained tissue sample may be recorded, preferably in a high resolution, for later examination or for sending this digitalize picture to a remote location for examination. Accordingly, in embodiments the present invention may provide for storing an image relevant to the process of staining tissue samples. This may include images both before and after staining or some other operation, of course. Also, this feature of the invention may provide for archiving images of the about to be stained or the stained tissue samples for later verification of the tissue sample analysis or the identification if this should it be required. Thus the invention may automatically facilitate a user activity such as those mentioned. To understand the various possibilities, the automatic facilitation may be of activities including, but not limited to, later accessing a historical image of a stained tissue sample, remotely accessing an image of a stained tissue sample, archiving an image of a stained tissue sample, later accessing a historical image of an unstained tissue sample, remotely accessing an image of an unstained tissue sample, archiving an image of an unstained tissue sample, and the like activities.

A sensor may be provided in some embodiments that may automatically identify information from one or more slides or reagent containers. In some embodiments, protocol information may be provided by the adaptive sample processing control system. The sample processing system may process one or more slides, or one or more batches of slides, concurrently, sequentially, or in any other temporal fashion, potentially in accordance with protocol information provided by a slide having a sample or provided by the adaptive sample processing control system. Sample batches or individual slides may be inserted or removed during processing protocol steps by the control and monitoring accomplished by the adaptive sample processing control system.

Another embodiment of the present invention that may achieve the foregoing and other objects of invention may comprise a method of sample processing, comprising the steps of: accessing at least one of a plurality of drawers, providing at least one sample carrier retainment assembly configured with at least one sample carrier, configuring at least one of the drawers with the at least one sample carrier retainment assemblies, and adaptively processing the sample carriers. The step of adaptive processing may automate the processing of samples and may allow for either or both continuous or batch processing of slides, and may afford multiple independent slide processing and in some embodiments redundant slide processing to process each slide independently.

Embodiments of the invention may further comprise a method of automated sample processing, comprising the steps of: acquiring protocol information, transmitting the protocol information to at least one sample processing system, adaptively processing samples, and acquiring sample processing information from the step of adaptively processing. Furthermore, embodiments may provide: maintaining the protocol information, maintaining the sample processing information, information sharing of protocol information, and sample processing information. These and other method steps may be provided for individual samples or multiple batch processing, sample diagnostic features, and real-time or adaptive capabilities for multiple batch processing.

Many aspects of invention are applicable to immunohistochemistry (IHC) techniques, as well as in-situ hybridization (ISH) and fluorescent in-situ hybridization (FISH) special staining of samples, and microarrays, especially techniques incorporating target retrieval or the staining of samples.

Support should be understood to exist for the following aspects and embodiments of the invention:
An automatic staining apparatus comprising:
at least one reagent container;
at least one sample;
a robotic element adapted to affect said reagent container and said sample;
a control element to which said robotic element is responsive; and
an image-capture 2-D optical sensor configured to two dimensionally image at least one element in said automatic staining apparatus.
A method of identifying at least one property in an automatic staining apparatus comprising the steps of:
providing at least one sample;
providing at least one reagent container;
providing a robotic element adapted to affect said reagent container and said sample;
optically sensing a two dimensional image of at least one element in said automatic staining apparatus;
recording relevant image data; and
feeding said image data to a control element to which said robotic element is responsive.
A method of staining samples in an automatic staining apparatus comprising the steps of:
providing at least one sample;
providing at least one reagent container;
providing a robotic element adapted to affect said reagent container and said sample;
providing an optical sensor responsive to said robotic element and adapted to sense a two dimensional image of at least one element in said automatic staining apparatus;
recording relevant image data; and
feeding said image data to a control element to which said robotic element is responsive.
An automatic staining apparatus comprising:
at least one reagent container;
at least one sample;
a robotic element adapted to affect said reagent container and said sample;
a control element to which said robotic element is responsive; and
a multifunction optical sensor configured to sense at least one element in said automatic staining apparatus.

BRIEF DESCRIPTION OF DRAWINGS

In the following the invention is described with reference to the accompanying drawings, in which.

MODE(S) FOR CARRYING OUT THE INVENTION

Figure 1:
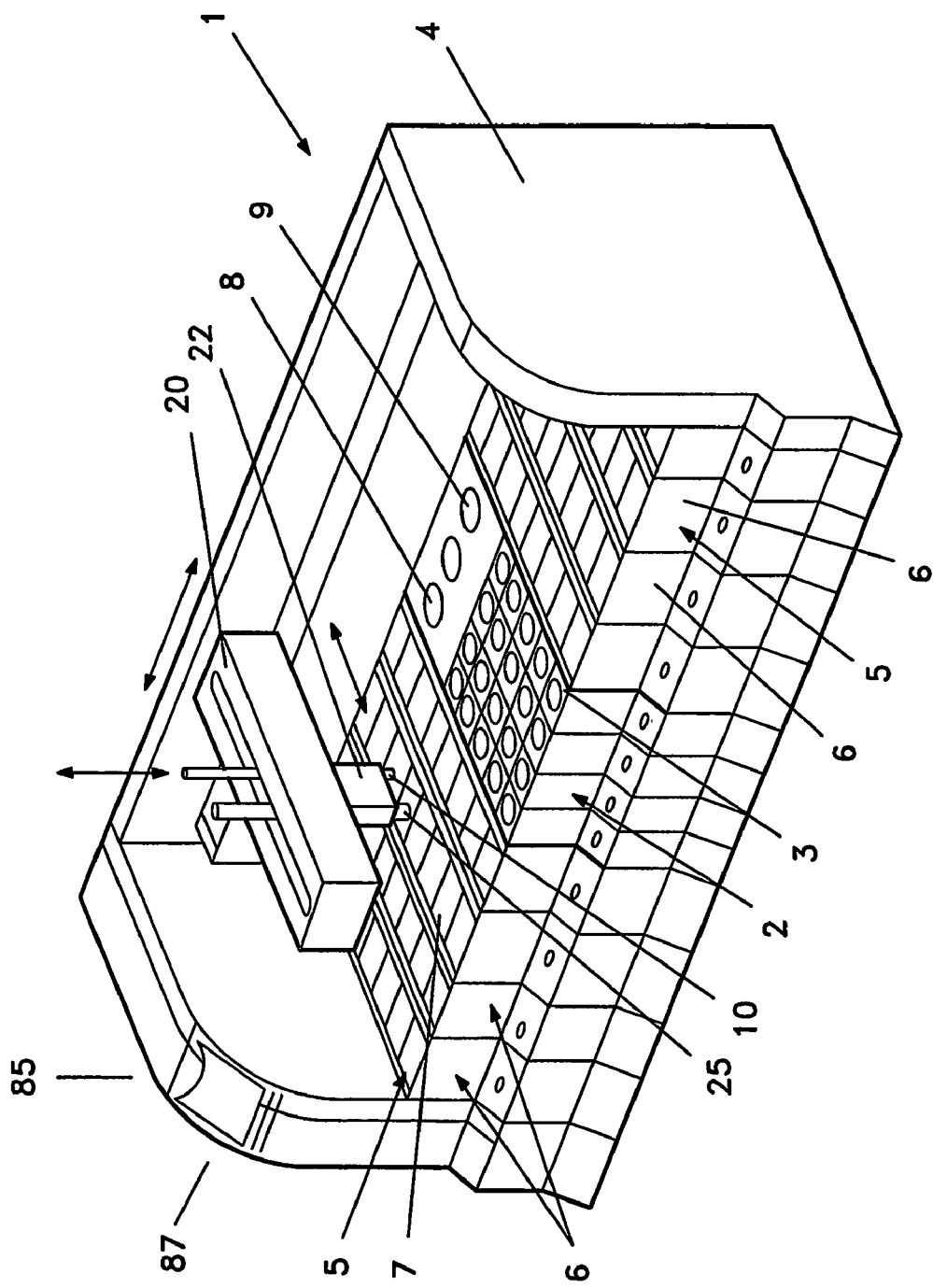
FIG. 1 is a schematic perspective view of a staining apparatus according to the preferred embodiment of the invention.
Figure 2:
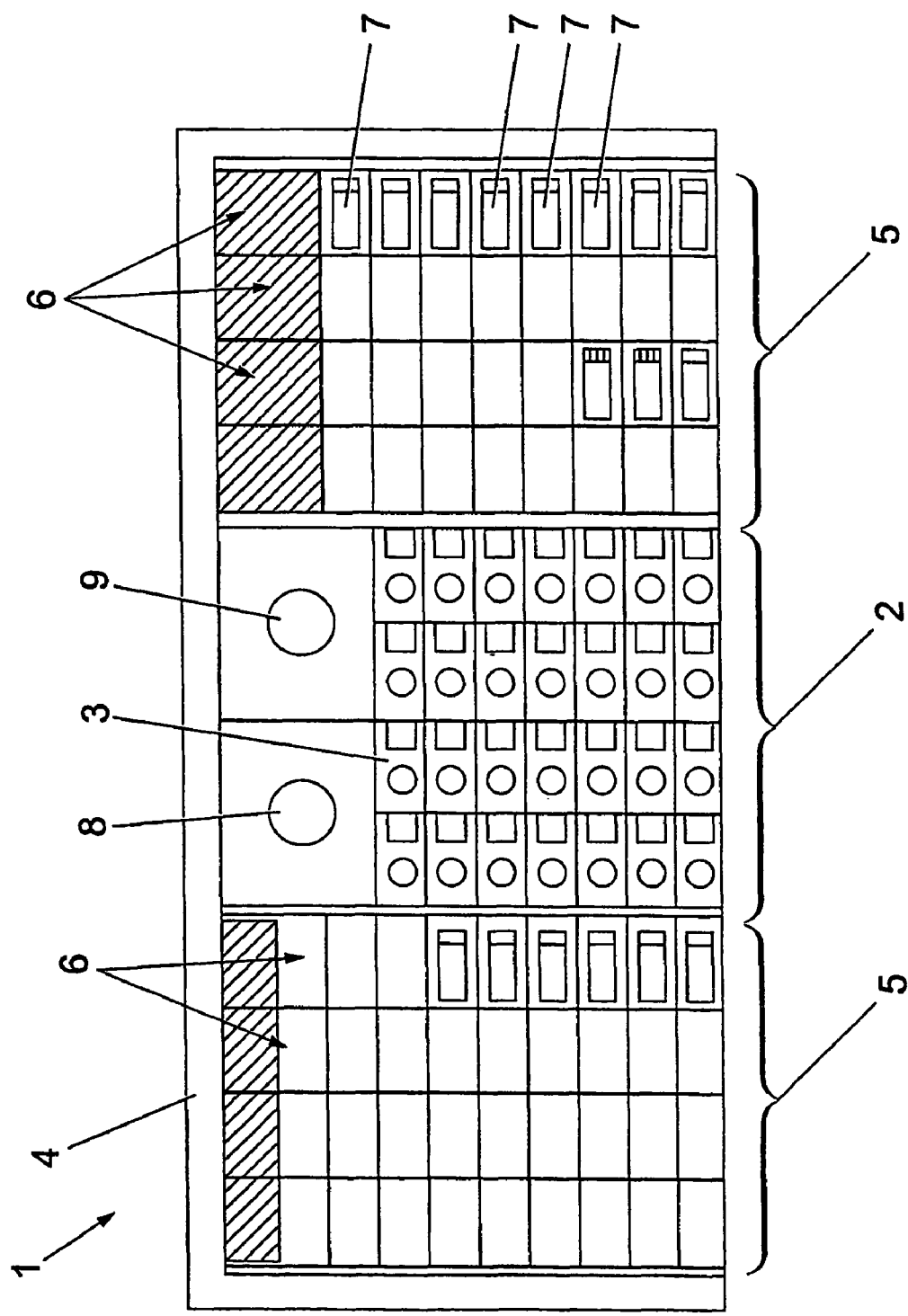
FIG. 2 is a top view of the work area in the staining apparatus shown in FIG. 1.

An automatic staining apparatus 1 according to the invention is shown in FIGS. 1 and 2. The automatic staining apparatus 1 comprises a rectangular frame 4 surrounding a reagent station or section 2 comprising an array of reagent bottle or container compartments, wherein each compartment a reagent vial or reagent container 3 is placed, and a first and second slide sections 5 wherein a number of separate racks 6 is placed, and where each rack 6 comprises a number of microscope slides 7 mounted side by side in the rack 6. A plurality of reagent containers or even slides may be placed in any desired order, an array. In the embodiment shown, each rack may hold up to 8 slides, but the rack may be designed to hold any suitable number of slides. With eight racks arranged side by side, the shown embodiments may hold up to 64 slides 7 each having a sample, e.g. a tissue mounted on the upper side of the slide, so that reagent may be applied from above to the sample on each slide. The sample processed may be any material, but is most likely a biologic material such as a biological sample or a biological specimen, perhaps such as a histological sample, e.g. tissue and cell specimens, cells, collections of cells, or tissue samples, the definition to include cell lines, proteins and synthetic peptides, tissues, cell preps, cell preparations, blood, bodily fluids, bone marrow, cytology specimens, blood smears, thin-layer preparations, and micro arrays. It should also be understood to include slide-based biological samples.

As mentioned, the present invention may include a robotic element, which may somehow affect the reagent container and tissue sample. Thus any sort of action to, action resulting from, or merely information from the reagent container or tissue sample may be facilitated through the robotic element. The robotic element, in embodiments, may be adapted to perform staining of the slides with (including as a result of or in conjunction with) the reagent application or the like. The robot arm or robotic element 20 may also remove reagent from a reagent container to a predetermined tissue sample. For example, a robotic element 20 for moving a probe 10 in X and Y (as well as Z) direction as indicated by the arrows X and Y is arranged above the frame 4 of the staining apparatus. A robot arm may position the probe 10 above all reagent vials 3 as well as above all the slides 7, and may further operate the probe 10 to aspirate portions of reagent contained in any of the vials 3, to transfer the portion of reagent and apply it to any of the slides 7 in order to provide a selected staining or treatment of the sample on each slide 7. A control element may manage a staining process by controlling the entire process or even any portion of it. By use of a suitable control element or alternatively a control means e.g. capability within a computer (not shown) having the appropriate software and input data for the purpose, this staining apparatus 1 may be able to automatically stain or treat samples requiring different staining or treatment reagents and processes.

Figure 3:
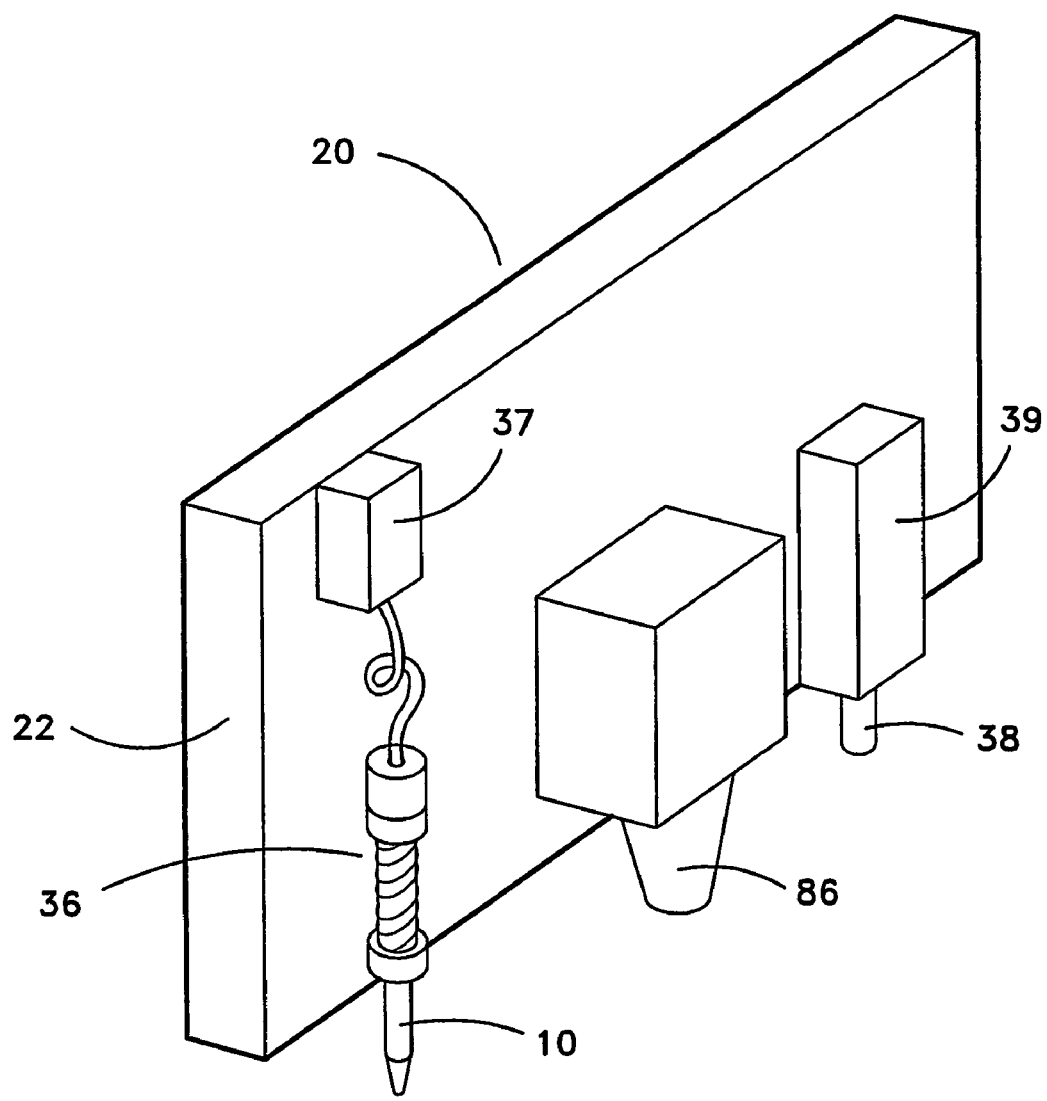
FIG. 3 is a detailed view of the robotic element in the staining apparatus according to some embodiments of the invention.

As shown in FIGS. 1 and 3, the probe 10 is accommodated in a robotic head 22 and is manipulated by the robotic element 20. The probe 10 is raised to an upper position (in a Z direction) where it is clear of the vials 3 underneath the probe 10, but the robot may include means or element in the robotic head 22 for lowering the probe 10 in order to dip the probe tip into the content of a selected reagent vial 3 and to aspirate a selected amount of reagent for the selected staining or treatment process. In an embodiment, the present invention may include providing an optical sensor 86 on a robotic element and perhaps moving the optical sensor to a predetermined position through action of the robotic element. As but one example, the robotic head 22 may be provided with an optical sensor 86, perhaps even a CCD camera 25 pointing downwards. An optical sensor may be positioned on or perhaps more broadly in response to the robotic element. After the optical sensor is positioned, image data may be recorded at the location at which the optical sensor is established.

In some embodiments a robotic element 20 or even a robotic head 22 may include a variety of components, including but not limited to a push tool 38 that may be connected to an air cylinder 39, a probe 10 that may be responsive to a probe movement element 36 which may even be connected to a syringe pump 37, and an optical sensor 86 as shown in FIG. 3.

In embodiments, the optical sensor may detect two-dimensional image data of a relevant property. It may also be adapted to sense a two-dimensional image of an element in general. The camera may be utilized to determine status information of the slides and the reagent bottles and other features of the apparatus in the work area, for example reading a code provided on a reagent container to determine the reagent type and the reagent location within the system. The camera may also determine status of the tissue sample carriers, for example the location of a particular slide, informational indicia, such as a code, that indicate information about the tissue sample presented on the slide or the processing protocol to be performed. A camera may be used for diagnostic purposes. In some embodiments, the sample may be scanned for further analysis, potentially by a computer. The present invention may include, in embodiments, a computer image biological analysis element or perhaps even biologically analysing image data of a sample with a computer.

As previously discussed, the invention may include recording a variety of relevant image data. Of course, a variety of relevant image data may be recorded.

Importantly, this may include recording element calibration reference points, or perhaps even robotic element calibration reference positions on or in the apparatus. As mentioned, the invention may also provide for recording slide identification image data and reagent identification image data. A significant aspect of an embodiment is the possibility of recording an optical identification element of a particular slide or perhaps merely recording information relevant to an element. Such information may include information concerning the tissue sample, of course. Similarly, optical identification may be recorded on a reagent container that may include information concerning the reagent contained therein. It may provide for recording a two-dimensional symbology on a slide or even on a reagent container. Two-dimensional symbology recorded on a slide may represent data including, but not limited to: tissue sample related data, patient identification data, staining protocol data, or the like. Two-dimensional symbology recorded on a reagent container may represent data including, but not limited to: reagent related data, reagent type data, reagent volume related data, reagent durability related data, or the like. It may also provide a connection element through which captured image data may be transferred to the control element. It may include feeding the image data to a control element so that the robotic element may respond. After the relevant image data has been recorded, and perhaps as a result of feeding that data to the control element, the invention may manipulate a staining or other process according to that relevant image data. Thus the invention may perform staining of slides according to tissue specific protocols.

The staining apparatus 1 of the present embodiment further comprises a probe washing station 8 and a reagent mixer 9, and the robotic element 20 is furthermore arranged to transfer the probe to the washing station 8 as well as to the reagent mixer 9.

Figure 4:
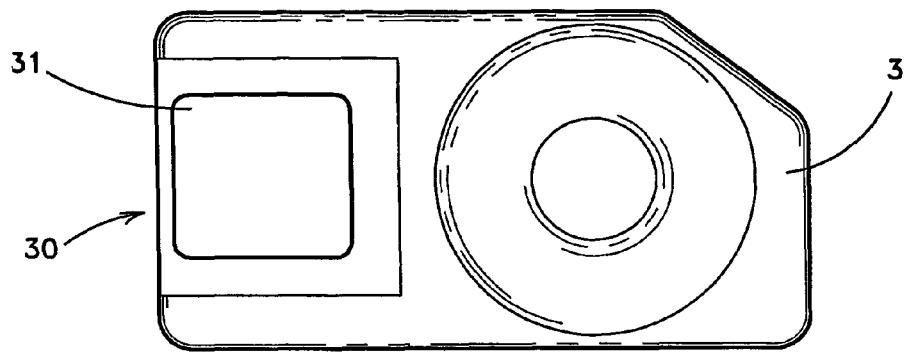
FIG. 4 is a top view of a reagent bottle with optical identification means.

As shown in FIG. 4, the reagent bottle 3 may be provided with an area 30 on a surface on which to mount an optical identification element. This optical identifier may be an adhesive label 31 carrying encoded information about the content of the bottle 3, such as reagent type, date of manufacture, expiry date, etc. The encoded information could be in the form of a data matrix code, an INFOGLYPH™ code or any other kind of 2-D code, and could in principle also be a simple 1-D code, i.e. a bar code. Additionally, the label 31 may also be provided with human readable text to aid the operator handling the reagent bottles e.g. during loading of bottles into the staining apparatus.

Figure 5:
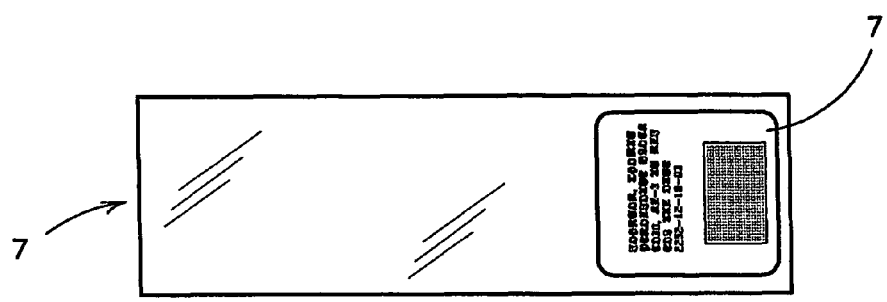
FIG. 5 is a microscope slide with an optical identifier label thereon.
Figure 6:
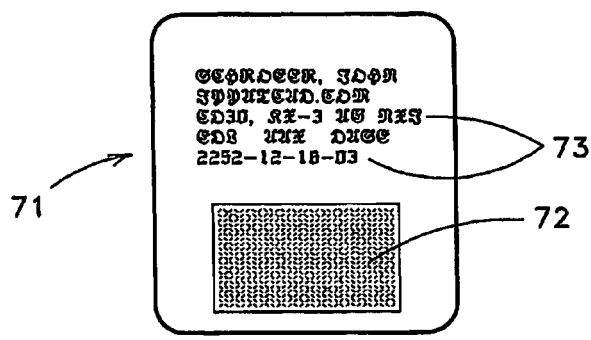
FIG. 6 is an example of a lay-out of this label.

FIG. 5 shows a slide 7 with a label 71 mounted thereon. One layout of the label 71 is shown in FIG. 6. The label 71 may be an adhesive optical identifier, which may be prepared for the particular slide and printed on a label printer (not shown) or any other suitable printing device. It is even possible that in a particular situation, if a batch of slides is to be subjected to the same treatment, a series of identical labels could be provided for the slides. The label 71 may comprise an area 72 for encoded information about the tissue sample on the slide 7, such as patient data, date and file number, the staining protocol and/or the series of process steps. Furthermore, the label 71 may be provided with one or more rows 73 of human readable text and/or blank space for the laboratory personnel preparing the slides to write on the slide label.

Figure 7:
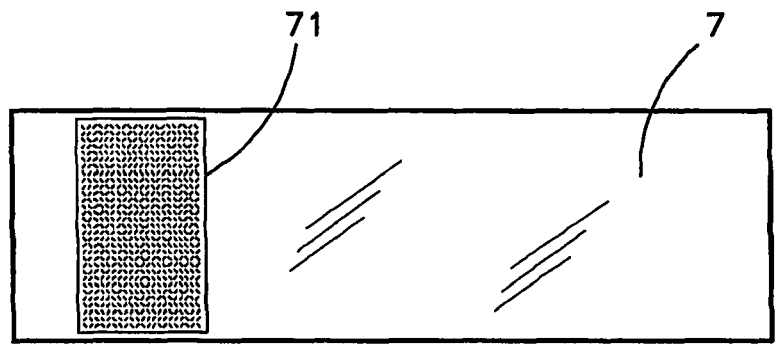
FIGS. 7 to 10 are examples of various kinds of optical identifying means on the slides.
Figure 8:
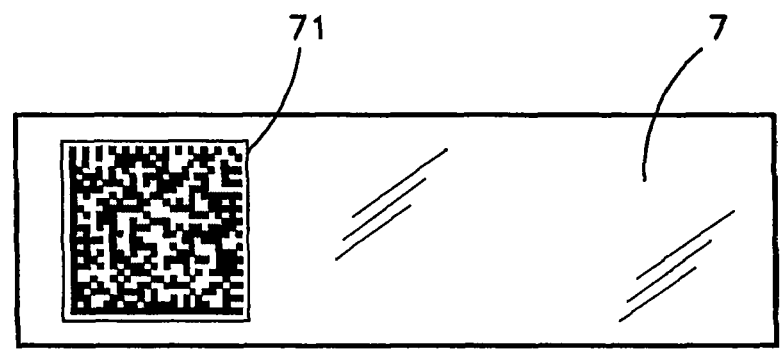
Figure 9:
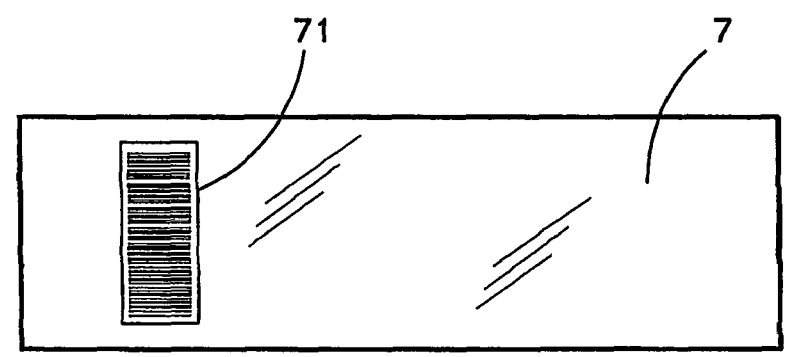

In FIGS. 7 to 9 various kinds of data encoded symbology for the label 71 (the entire label 71 as shown or only for the label area 72 (see FIG. 6)).

In FIG. 7, an example of a 2-D symbology of the INFOGLYPH™ type is shown. This may include perhaps even an information carpet type of symbology. This type of 2-D symbology is advantageous since it can carry a large amount of optically machine-readable information. Making use of a high-resolution camera, this type of symbology may be readable in a high resolution and a large amount of information can be encoded therein. The symbology may be printed with tiny diagonal lines in different directions or perhaps even colors and can easily be read by a CCD camera or the like.

FIG. 8 shows an example of a data matrix code that can be used as an alternative to the INFOGLYPH™ symbology. The data matrix is similarly readable with a CCD camera but may not carry as many data in the encoding as the INFOGLYPH™. However, it is easier to print as it may have a less high resolution making it a simple and cost effective solution if less identification data on the slides and the reagent bottles is required. A yet simpler solution is shown in FIG. 9, where the symbology is the old bar code. In principle this means that only a bar code scanner is required for reading the slides and the reagent bottle information, but by using a 2-D sensor, the possibility of self-calibration and monitoring the installation of slides and reagents in the staining apparatus may be enhanced.

In an embodiment, the optical identifiers on the slides and on the reagent bottles are the same type. This may facilitate the image processing of the identification process in the staining apparatus.

Figure 10:
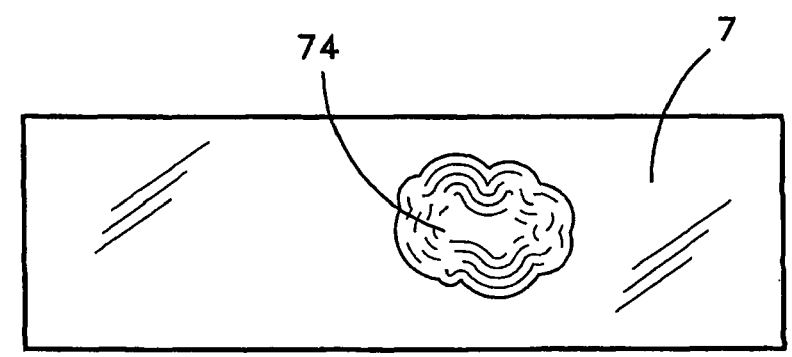

A different approach to identifying the individual slides or as a way of facilitating the new capabilities of confirming identification or storing confirmatory information may be to record the contour and/or the texture of the tissue sample 74 itself, such as shown in FIG. 10. Utilizing the high-resolution of the image that can be recorded by the camera, the unique features of the tissue sample itself can be used as a graphical identifier of the slide. Furthermore, an image of the stained tissue sample can be recorded so that a digital representation of the tissue sample is produced. This digital image can be sent electronically to remote locations for instant examination and/or archived for later examination. This may provide the staining apparatus with a unique flexibility in use and may introduce new and advantageous methods of analyzing the tissue samples.

Besides identifying the microscope slides and the reagent bottles in the staining apparatus, the 2-D optical sensor can also be used for self-calibration of the apparatus, e.g. after maintenance, if the apparatus has been disassembled or moved to another location. By identifying critical locations within the apparatus by capturing an image by the camera, the image processing software can compare the captured image with a reference image to determine if certain critical components in the apparatus are off-set from their predetermined positions, e.g. if a slide rack or a slide is slightly off-set, and if so, a set of correction data for the robotic motion control system may be calculated and this set of data may be used for calibrating the apparatus. If the correction needed exceeds a certain size, a warning could be automatically issued to an operator, so that it is ensured that the apparatus does not malfunction during the processing of the slides. Furthermore, this image analysis system could also be used for determining if a slide is present or dislocated in the rack in order to produce a warning signal.

By the invention, it is realised that a variety of changes of the above description of some preferred embodiments of the invention may be made without departing from the scope of the invention as set forth in the claims. As can be easily understood, the basic concepts of the present invention may be embodied in a variety of ways. It involves both staining techniques as well as various systems, assemblies, and devices to accomplish staining and other functions. In this application, the staining techniques are also disclosed as part of the results shown to be achieved by the various systems, assemblies, and devices described and as steps that are inherent to utilization. They should be understood to be the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The reader should be aware that the specific discussion may not explicitly describe all embodiments possible; many alternatives are implicit. It also may not fully explain the generic nature of the invention and may not explicitly show how each feature or element can actually be representative of a broader filmation or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the disclosure.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon to support additional claims for presentation in this or subsequent patent application.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sensor" should be understood to encompass disclosure of the act of "sensing"—whether explicitly discussed or not—and, conversely, were there effectively disclosure of the act of "sensing", such a disclosure should be understood to encompass disclosure of a "sensor" and even a "means for sensing". It should also be understood that in jurisdictions where specific language may be construed as limiting, as but one example in the United States where some interpretations of "means for" elements can be construed narrowly, broader equivalent language (such as "element" or the like) may be used to avoid the narrow interpretation and should be understood as encompassed by this specification. Such changes and alternative terms are to be understood to be explicitly included in the description.

Any patents, patent applications, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, any priority case for this application is hereby appended and hereby incorporated by reference.

Thus, the applicant(s) should be understood to have support to claim at least: i) each of the sample processing systems and subsystems as herein disclosed and described, ii) the related methods disclosed and described, iii) similar, equivalent, and even implicit variations of each of these systems, assemblies, devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and systems, assemblies, devices, and apparatuses substantially as described hereinbefore and with reference to any of the accompanying examples, x) the various combinations and permutations of each of the elements disclosed, xi) each potentially dependent claim or concept as a dependency on each and every one of the independent claims or concepts presented, xii) processes performed with the aid of or on a computer as described throughout the above discussion, xiii) a programmable system as described throughout the above discussion, xiv) a computer readable memory encoded with data to direct a computer comprising means or elements which function as described throughout the above discussion, xv) a computer configured as herein disclosed and described, xvi) individual or combined subroutines and programs as herein disclosed and described, xvii) the related methods disclosed and described, xviii) similar, equivalent, and even implicit variations of each of these systems and methods, xix) those alternative designs which accomplish each of the functions shown as are disclosed and described, xx) those alternative designs and methods which accomplish each of the functions shown as are implicit to accomplish that which is disclosed and described, xxi) each feature, component, and step shown as separate and independent inventions, and xxii) the various combinations and permutations of each of the above.

Further, if or when used, the use of the transitional phrase "comprising" or the like is used to maintain the "open-end" claims herein, according to traditional claim interpretation. Thus, unless the context requires otherwise, it should be understood that the term "comprise" or variations such as "comprises" or "comprising" or the like, are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An automatic staining apparatus comprising:
    at least one removable reagent container positioned on a reagent rack within a reagent section;
    at least one slide positioned within a slide section;
    wherein a robotic element is configured to move above the reagent section and above the slide section during a staining process and wherein the reagent rack is removable below the plane of the robotic element;
    wherein the reagent section is situated to enable the at least one removable reagent container to be added to or removed from the apparatus without interrupting the movement of the robotic element during dispensing of at least one reagent during the staining process;

wherein the robotic element comprises an optical sensor configured to automatically identify new slides and reagent bottles loaded into the apparatus during the staining process; and a control element to which the robotic element is responsive, the control element configured to monitor insertion or removal of the at least one removable reagent container during the staining process and to continue movement of the robotic element and dispensing of at least one reagent during insertion or removal of the at least one removable reagent container.

2. An apparatus according to claim 1, wherein the optical sensor is adapted to locate pre-selected reference features for self-calibration of the robotic element.

3. An apparatus according to claim 1, wherein a sample is placed on the at least one slide, and wherein the optical sensor is adapted to record an image of the finalized sample after said sample has been subjected to the staining process.

4. An apparatus according to claim 3, further comprising:

at least one element provided on the at least one removable reagent container and the at least one slide;

wherein at least one element comprises an element selected from a group consisting of: a two-dimensional high-resolution symbology code, a datamatrix code, a bar code, an adhesive label, a two dimensional symbology zone, and a human readable text zone.

5. An apparatus according to claim 3, wherein the optical sensor is configured to identify a feature selected from a group consisting of: the texture of the sample, the outline of the sample, a visual property of the sample, and an individual identification feature of the sample.

6. A method of identifying at least one property in an automatic staining apparatus comprising the steps of:

providing at least one sample on a slide positioned within a slide section;

providing at least one reagent container positioned on a reagent rack within a reagent section;

wherein a robotic element is configured to move above the slide section and above the reagent section during a staining process and wherein the reagent rack is removable below the plane of the robotic element;

wherein the at least one reagent container is added to or removed from the apparatus without interrupting dispensing of at least one reagent during the staining process;

providing the robotic element with an optical sensor configured to automatically identify new slides and reagent bottles loaded into the apparatus during the staining process;

recording relevant image data;

recording calibration reference points of the apparatus; and feeding said image data to a control element to which said robotic element is responsive, the control element configured to monitor insertion or removal of the at least one reagent container during the staining process and to continue movement of the robotic element and dispensing of at least one reagent during insertion or removal of the at least one removable reagent container.

7. A method of staining samples in an automatic staining apparatus comprising the steps of:

providing at least one sample on a slide, the slide being positioned in a slide section within slide racks;

providing at least one reagent container positioned on a reagent rack within a reagent section;

wherein a robotic element is configured to move above the slide section and above the reagent section during a staining process and wherein the reagent rack is removable below the plane of the robotic element;

wherein the at least one reagent container is added to or removed from the apparatus without interrupting dispensing of at least one reagent during the staining process;

providing the robotic element with an optical sensor configured to automatically identify new slides and reagent bottles loaded into the apparatus during the staining process;

recording relevant image data;

recording calibration reference positions for said slide racks; and feeding said image data to a control element to which said robotic element is responsive, the control element configured to monitor insertion or removal of the at least one reagent container during the staining process and to continue movement of the robotic element and dispensing of at least one reagent during insertion or removal of the at least one removable reagent container.

8. An automatic staining apparatus comprising:

at least one reagent container positioned on a reagent rack within a reagent section;

at least one sample on a slide, the slide being positioned within a slide section;

wherein a robotic element is configured to move above the reagent section and above the slide section during a staining process and wherein the reagent rack is removable below the plane of the robotic element;

wherein the reagent section is situated to enable the at least one reagent container to be added to or removed from the apparatus without interrupting the movement of the robotic element during dispensing of at least one reagent during the staining process;

wherein the robotic element comprises an optical sensor configured to automatically identify new slides and reagent bottles loaded into the apparatus during the staining process and locate pre-selected reference features for self-calibration of the robotic element; and a control element to which the robotic element is responsive, the control element configured to monitor insertion or removal of the at least one reagent container during the staining process and to continue movement of the robotic element and dispensing of at least one reagent during insertion or removal of the at least one removable reagent container.

9. An automatic staining apparatus comprising:

at least one reagent container on a reagent rack in a reagent section;

at least one first sample contained on a slide in a first slide section;

at least one second sample contained on a slide in a second slide section, wherein said first slide section and said second slide section are separated by said reagent section;

wherein a robotic element is configured to move above the reagent section and above the first and second slide sections during a staining process and wherein the reagent rack is removable below the plane of the robotic element;

wherein the reagent section is situated to enable the at least one reagent container to be added to or removed from the apparatus without interrupting the movement of the robotic element during dispensing of at least one reagent during the staining process; and a control element to which said robotic element is responsive, the control element configured to monitor insertion or removal of the at least one reagent container during the staining process and to continue movement of the robotic element and dispensing of at least one reagent during insertion or removal of the at least one removable reagent container.

10. An automatic staining apparatus comprising:
at least one reagent container positioned on a reagent rack within a reagent section;
at least one sample placed on a slide, the slide being positioned within a slide section;
wherein a robotic element is configured to move above the reagent section and above the slide section during a staining process and wherein the reagent rack is removable below the plane of the robotic element;
wherein the reagent section is situated to enable the at least one reagent container to be added to or removed from the apparatus without interrupting the movement of the robotic element during dispensing of at least one reagent during the staining process;
wherein the robotic element comprises an optical sensor configured to automatically identify new slides and reagent bottles loaded into the apparatus during the staining process and image at least one optical identification element; and
a control element to which the robotic element is responsive, the control element configured to monitor insertion or removal of the at least one reagent container during the-staining process using the optical identification element and to continue movement of the robotic element and dispensing of at least one reagent during insertion or removal of the at least one removable reagent container.

11. An apparatus according to claim 10 wherein the optical identification element has reiterated information, said reiterated information comprises multiple reiterated information.

12. An apparatus according to claim 11 wherein said reiterated information comprises redundant information.

13. An apparatus according to claim 11 wherein said optical identification element comprises a two-dimensional high-resolution symbology code.

14. An apparatus according to claim 11 wherein said optical identification element comprises a datamatrix code.

15. An apparatus according to claim 11 wherein said optical identification element comprises a bar code.

16. An automatic staining apparatus comprising:
at least one reagent container positioned on a reagent rack within a reagent section;
at least one sample on a slide, the slide being positioned within a slide section;
wherein a robotic element is configured to move above the reagent section and above the slide section during a staining process and wherein the reagent rack is removable below the plane of the robotic element;
wherein the reagent section is situated to enable the at least one reagent container to be added to or removed from the apparatus without interrupting the movement of the robotic element during dispensing of at least one reagent during the staining process;
wherein the robotic element comprises an optical sensor configured to automatically identify new slides and reagent bottles loaded into the apparatus during the staining process;
a computer image biological analysis element; and
a control element to which the robotic element is responsive, the control element configured to monitor insertion or removal of the at least one reagent container during the staining process,
wherein the optical sensor records a first image of the at least one sample before staining and records a second image of the sample after staining and to continue movement of the robotic element and dispensing of at least one reagent during insertion or removal of the at least one removable reagent container.

17. An apparatus according to claim 16 wherein said optical sensor comprises a camera.

18. An apparatus according to claim 17, wherein said camera comprises a CCD element.

19. A method of identifying at least one property in an automatic staining apparatus comprising the steps of:
providing at least one sample, the sample being placed on a slide in a removable slide rack, the slide rack being positioned within a slide section;
providing at least one reagent container positioned on a reagent rack within a reagent section;
wherein a robotic element is configured to move above the reagent section and above the slide section during a staining process and wherein the reagent rack is removable below the plane of the robotic element;
wherein the at least one reagent container is added to or removed from the apparatus without interrupting dispensing of at least one reagent during the staining process;
providing the robotic element with an optical sensor configured to automatically identify new slides and regent bottles loaded into the apparatus during the staining process;
recording relevant image data;
feeding said image data to a control element to which said robotic element is responsive, the control element configured to monitor insertion or removal of the at least one reagent container during the staining process and to continue movement of the robotic element and dispensing of at least one reagent during insertion or removal of the at least one removable reagent container; and
biologically analysing image data of said at least one sample with a computer.

20. A method according to claim 19, wherein said optical sensor comprises a camera.

21. A method according to claim 20, wherein said camera comprises a CCD element.

22. A method of staining tissue samples in an automatic staining apparatus comprising the steps of:
providing at least one removable sample on at least one slide positioned within a slide section;
providing at least one reagent container positioned on a reagent rack within a reagent section;
wherein a robotic element is configured to move above the reagent section and above the slide section during a staining process and wherein the reagent rack is removable below the plane of the robotic element;
wherein the at least one reagent container is be added to or removed from the apparatus without interrupting dispensing of at least one reagent during the staining process;
providing the robotic element with an optical sensor configured to automatically identify new slides and reagent bottles loaded into the apparatus during the staining process;
recording relevant image data;
feeding said image data to a control element to which said robotic element is responsive, the control element configured to monitor insertion or removal of the at least one reagent container during the staining process and to continue movement of the robotic element and dispensing of at least one reagent during insertion or removal of the at least one removable reagent container; and biologically analysing image data of said at least one sample with a computer.

23. A method according to claim 22, wherein said optical sensor comprises a camera.

24. A method according to claim 22, wherein said optical sensor comprises a CCD element.

25. A method according to claim 22, further comprising a step of storing an image relevant to the staining process.

26. An automatic staining apparatus comprising:
at least one reagent container positioned on a reagent rack within a reagent section;
at least one sample, the sample being placed on a slide positioned within a slide section;
wherein a robotic element is configured to move above the reagent section and above the slide section during a staining process and wherein the reagent rack is removable below the plane of the robotic element;
wherein the reagent section is situated to enable the at least one reagent container to be added to or removed from the apparatus without interrupting the movement of the robotic element during dispensing of at least one reagent during the staining process;
wherein the robotic element comprises a multifunction optical sensor configured to automatically identify new slides and reagent bottles loaded into the apparatus during the staining process;
a computer image biological analysis element; and
a control element to which the robotic element is responsive, the control element configured to monitor insertion or removal of the at least one reagent container during the staining process and to continue movement of the robotic element and dispensing of at least one reagent during insertion or removal of the at least one removable reagent container.

27. An apparatus according to claim 26, wherein said optical sensor comprises a camera.

28. An apparatus according to claim 26, wherein said optical sensor comprises a CCD element.

29. An apparatus according to claim 26, further comprising a stored image relevant to the staining process.

30. An automatic staining apparatus comprising:
at least one removable reagent container positioned on a reagent rack within a reagent section;
at least two staining sections separated by the reagent section;
at least one sample placed on a slide in a slide rack, the slide rack being positioned within the staining sections;
wherein a robotic element is configured to move above the reagent section and above the staining sections during a staining process and wherein the reagent rack is removable below the plane of the robotic element;
wherein the reagent section is situated to enable the at least one reagent container to be added to or removed from the apparatus without interrupting the movement of the robotic element during dispensing of at least one reagent during the staining process;
wherein the robotic element comprises an optical sensor configured to automatically identify new slides and reagent bottles loaded into the apparatus during the staining process; and
a control element to which the robotic element is responsive, the control element configured to monitor insertion or removal of the at least one removable reagent container during the staining process and to continue movement of the robotic element and dispensing of at least one reagent during insertion or removal of the at least one removable reagent container.

31. A method of staining tissue samples in an automatic staining apparatus comprising the steps of:
providing at least one slide positioned within a slide section;
providing at least one removable reagent container positioned on a reagent rack within a reagent section;
wherein a robotic element is configured to move above the reagent section and above the slide section during a staining process and wherein the reagent rack is removable below the plane of the robotic element;
wherein the at least one reagent container is be added to or removed from the apparatus without interrupting dispensing of at least one reagent during the staining process;
providing the robotic element with an optical sensor configured to automatically identify new slides and reagent bottles loaded into the apparatus during the staining process;
recording relevant image data; and
feeding said image data to a control element to which said robotic element is responsive, the control element configured to monitor insertion or removal of the at least one removable reagent container during the staining process and to continue movement of the robotic element and dispensing of at least one reagent during insertion or removal of the at least one removable reagent container.

* * * * *

UNITED STATES PATENT AND TRADEMARK OFFICE
CERTIFICATE OF CORRECTION

PATENT NO. : 8,257,968 B2  
APPLICATION NO. : 10/538964  
DATED : September 4, 2012  
INVENTOR(S) : Doug Sweet et al.

Page 1 of 1

It is certified that error appears in the above-identified patent and that said Letters Patent is hereby corrected as shown below:

In the Claims

Claim 4, Column 15, Line 25, "datamatrix" should read --data matrix--.

Claim 10, Column 17, Line 29, "the-staining" should read --the staining--.

Claim 14, Column 17, Line 42, "datamatrix" should read --data matrix--.

Claim 19, Column 18, Line 38, "analysing" should read as --analyzing--.

Claim 22, Column 19, Line 3, "analysing" should read as --analyzing--.

Claim 31, Column 20, Line 31, "is be" should read --is to be--.

Signed and Sealed this  
Twentieth Day of May, 2014

Michelle K. Lee  
*Deputy Director of the United States Patent and Trademark Office*